United States Patent
Eifler

(10) Patent No.: US 11,883,597 B2
(45) Date of Patent: Jan. 30, 2024

(54) RESPIRATORY MASK AND PROCESS FOR MAKING A RESPIRATORY MASK

(71) Applicant: Loewenstein Medical Technology S.A., Luxembourg (LU)

(72) Inventor: Martin Eifler, Glueckstadt (DE)

(73) Assignee: LOEWENSTEIN MEDICAL TECHNOLOGY S.A., Luxembourg (LU)

( * ) Notice: Subject to any disclaimer, the term of this patent is extended or adjusted under 35 U.S.C. 154(b) by 615 days.

(21) Appl. No.: 16/506,276

(22) Filed: Jul. 9, 2019

(65) Prior Publication Data

US 2020/0016355 A1    Jan. 16, 2020

(30) Foreign Application Priority Data

Jul. 12, 2018  (DE) .......................... 102018005517.6

(51) Int. Cl.
*A61M 16/00* (2006.01)
*A61M 16/06* (2006.01)

(52) U.S. Cl.
CPC ......... *A61M 16/06* (2013.01); *A61M 2205/42* (2013.01); *A61M 2207/00* (2013.01)

(58) Field of Classification Search
CPC .......... A61M 2207/00; A61M 2205/42; A61M 2206/20; A61M 16/06–0655; A61M 2016/0661; A61M 16/0683–0694; A61M 16/0666–0677; A62B 18/00; A62B 18/02–06; A62B 18/10
See application file for complete search history.

(56) References Cited

U.S. PATENT DOCUMENTS

| | | | |
|---|---|---|---|
| 8,397,727 B2 * | 3/2013 | Ng | A61M 16/0816 128/206.24 |
| 2008/0072910 A1 | 3/2008 | Janbakhsh et al. | |
| 2009/0050156 A1 * | 2/2009 | Ng | A61M 16/0816 128/205.24 |
| 2011/0011397 A1 | 1/2011 | Ziv et al. | |
| 2012/0067349 A1 | 3/2012 | Barlow et al. | |
| 2013/0213401 A1 | 8/2013 | Haibach | |
| 2013/0327336 A1 * | 12/2013 | Burnham | A61M 16/0816 128/206.21 |
| 2014/0150798 A1 * | 6/2014 | Fong | A61M 16/0825 128/206.21 |
| 2016/0008558 A1 | 1/2016 | Huddart et al. | |

(Continued)

FOREIGN PATENT DOCUMENTS

DE    102005041717 A1    4/2006
EP        2027880 A1    2/2009
(Continued)

*Primary Examiner* — Philip R Wiest
*Assistant Examiner* — Sarah B Lederer
(74) *Attorney, Agent, or Firm* — Abel Schillinger, LLP

(57) ABSTRACT

The invention relates to a respiratory mask (1) having a mask unit (2) and having an emission device (3) for discharging exhaled gas from the respiratory mask (1). The mask unit (2) comprises a mask body (4) and a connection unit (5) which can be connected to the mask body (4) for connection of a respiratory gas feed line (101). The emission device (3) comprises a plurality of flow channels (6), which are arranged in at least one part of the mask unit (2). Here the emission device (3) comprises at least one flow channel.

18 Claims, 21 Drawing Sheets

(56) References Cited

U.S. PATENT DOCUMENTS

| | | |
|---|---|---|
| 2018/0185597 A1 | 7/2018 | Ewers et al. |
| 2018/0264222 A1 | 9/2018 | Dantanarayama et al. |
| 2019/0209804 A1 | 7/2019 | Dantanarayama et al. |

FOREIGN PATENT DOCUMENTS

| | | |
|---|---|---|
| EP | 2979719 A1 | 2/2016 |
| WO | 2010139014 A1 | 12/2010 |
| WO | 2011003130 A1 | 1/2011 |
| WO | 2013006899 A1 | 1/2013 |
| WO | 2014129913 A1 | 8/2014 |
| WO | 2017049358 A1 | 3/2017 |
| WO | 2018053589 A1 | 3/2018 |

\* cited by examiner

RESPIRATORY MASK AND PROCESS FOR MAKING A RESPIRATORY MASK

CROSS-REFERENCE TO RELATED APPLICATIONS

The present application claims priority under 35 U.S.C. § 119 of German Patent Application No. 10 2018 005 517.6, filed on Jul. 12, 2018, the entire disclosure of which is expressly incorporated by reference herein.

BACKGROUND OF THE INVENTION

1. Field of the Invention

The present invention relates to a respiratory mask and to a process for producing such a respiratory mask. The respiratory mask comprises at least one mask unit and at least one emission device for discharging exhaled gas from the respiratory mask. The emission device comprises a multiplicity of flow channels, which are arranged in at least one part of the mask unit.

2. Discussion of Background Information

In respiratory masks for so-called single-tube systems, the exhaled air is generally discharged directly from the respiratory mask into the atmosphere, or into the surroundings. However, the emission of the exhaled gas, or of the exhaled air, from the respiratory mask often leads to unpleasant noises. When the air impinges on the face of the patient or the person in bed next to them, this is often perceived as very unpleasant. Noises and air flows are a particular problem when the respiratory mask is being used for sleep therapy.

DE102005041717A1, the entire disclosure of which is incorporated by reference herein, discloses a respiratory mask having a connection unit for a respiratory gas tube and, next to the connection unit in the respiratory mask, an emission device for discharging exhaled gas. The emission device comprises a multiplicity of flow channels, which are arranged in an annular gap in the mask body and are partially covered by a cover ring, so that an exhalation gap is formed. A disadvantage in this case is, in particular, the two-part construction.

EP2027880B1, the entire disclosure of which is incorporated by reference herein, discloses a respiratory mask having a connection unit for a respiratory gas tube and, in the connection unit, an emission device for discharging exhaled gas. The emission device comprises a multiplicity of flow channels, which are at least partially covered in one exemplary embodiment. A disadvantage in this case is the arrangement in the connection unit.

It would therefore be advantageous to be capable of reducing or avoiding undesired noises and air flows when discharging exhaled gas from a respiratory mask. In this case, the respiratory mask should preferably also be producible in a cost-optimized way, in order to be available for as many users or patients as possible.

SUMMARY OF THE INVENTION

The respiratory mask according to the invention is intended, in particular, for a respirator apparatus and/or for a sleep therapy apparatus. The respiratory mask comprises at least one mask unit and at least one emission device for discharging exhaled gas from the respiratory mask. The mask unit comprises at least one mask body and at least one connection unit which can be connected to the mask body for connection of a respiratory gas line.

The respiratory mask according to the invention comprises a mask unit having at least one emission device for discharging exhaled gas from inside the respiratory mask, the mask unit comprising at least one mask body and at least one mask bead connected to the mask body and a connection unit connected to the mask body for connection of a respiratory gas feed line, and the emission device comprising a multiplicity of separate flow channels, the emission device comprising a plurality of separate flow channels which respectively consist of at least two flow subchannels, the flow channels being arranged at a distance from one another and at least in sections circularly or semicircularly.

The emission device comprises a multiplicity of flow channels which are arranged in at least one part of the mask unit. The emission device in this case comprises, for example, at least nine flow channels.

In particular, two or preferably a multiplicity of flow channels are provided with flow subchannels. In this way, particularly advantageous flow properties can be achieved. In particular, all or at least a majority of the flow channels comprise at least two flow subchannels. The flow subchannels, which form a flow channel, are in this case for example configured geometrically differently. The flow channels therefore comprise geometrically different subsections.

At least one of the flow channels preferably has a varying channel cross section. Preferably, at least one flow channel has at least two different channel cross sections. Noises and undesired flows can therefore be particularly advantageously suppressed. It is also possible and preferred for the channel cross section to be configured unvaryingly.

It is preferred for at least one of the flow channels to be configured at least in sections conically and/or in the shape of a cone. In this way, particularly advantageous flow properties are achieved. In particular, at least one of the flow channels is configured at least in sections in the shape of a funnel.

Particularly preferably, at least one shoulder is arranged in at least one of the flow channels. Such a shoulder offers a straightforward and at the same time effective possibility for reducing noises and impinging flows. In particular, the shoulder provides at least one flow subchannel or is configured as such. The shoulder may comprise at least one elevation and/or depression and/or step or the like, or be configured as such.

The emission device is, for example, arranged in the mask body or in the connection unit.

The emission device is, for example, arranged at an interface between the mask body and the connection unit.

The emission device is, for example, formed integrally as part of the mask body or of the connection unit.

The emission device is, for example, manufactured as a separate component, which is integrated into the mask body or into the connection unit.

The emission device defines a plane E3 and the mask body or the connection unit defines a plane E4.

The planes E3 and E4 are at a distance from one another or coincide.

If the planes E3 and E4 are at a distance from one another and are materially connected to one another by a shoulder, the flow channels are arranged in the shoulder.

The planes E3 and E4 may extend inclined to one another or extend parallel to one another.

In one particularly advantageous configuration, at least one of the flow channels comprises at least one constriction section. In particular, the constriction section extends over at least one distance. In particular, an elongate constriction section is provided. By such a constriction section, the flow properties, and for example flow velocity and pressure, may be influenced particularly advantageously. In particular, the constriction section provides at least one flow subchannel or is configured as such.

In particular, the distance of the constriction section is equal to at least about one eighth of the total length of the flow channel. Preferably, the distance is at least about one sixth or at least about one fifth and particularly preferably at least about one fourth or at least about one third of the total length of the flow channel. It is also possible for the distance to be at least about half of the total length of the flow channel. The distance may also be at least about two thirds or about three fourths or also about nine tenths or more of the total length of the flow channel. The distance may also be configured to be shorter. A point-like constriction section is possible and preferred. The constriction section may comprise one or two or more constrictions. The flow channel may also be equipped with two or three or more constriction sections.

Particularly preferably, at least one of the flow channels comprises at least one inlet region narrowing in the shape of a funnel before the constriction section in the flow direction. It is also particularly preferred for at least one of the flow channels to comprise at least one outlet region widening in the shape of a funnel after the constriction section in the flow direction. Such configurations offer a particularly advantageous adaptation of pressure conditions and flow velocities. Thus, noises may be reduced significantly and undesired impinging flows may be substantially avoided. A funnel-like region is, in particular, intended to mean a successively or varyingly increasing or decreasing channel cross section. The inlet region and/or the outlet region are in particular configured in the shape of a funnel, or as a funnel.

The inlet region is in this case arranged in the inner region of the respiratory mask, facing toward the face of the patient, and the outlet region, arranged opposite the inlet, opens to the ambient air.

At least one flow channel has a length, starting with the inlet region, as far as the outlet region, of about 0.5 to 5 mm, preferably about 0.8-3 mm. The length of the flow channel in this case preferably spans the emission device, or the mask body, starting with the inlet region as far as the outlet region.

At least one flow channel has (in cross section) a diameter or an edge length of about 0.1 to 0.9 mm, preferably about 0.3-7 mm, particularly preferably about 0.4-0.6 mm.

At least one of the flow channels may comprise at least in sections a channel cross section with a quadrilateral cross-sectional profile. In particular, the quadrilateral cross-sectional profile has rounded corners. Preferably, the quadrilateral cross-sectional profile is configured rectangularly. Such a cross-sectional profile is particularly advantageous with a view both to production and to the flow behavior. It is also possible for the quadrilateral cross-sectional profile to be configured squarely. A triangular or polygonal cross-sectional profile may also be provided. A round or oval, and for example elliptical, cross-sectional profile is also possible. The channel cross section may also have a cross-sectional profile with a different geometry. For example, a cross-shaped cross-sectional profile may be provided.

Preferably, at least one of the flow channels extends obliquely in the mask unit. It is also preferred for at least two of the flow channels to extend obliquely with respect to one another. Such a configuration offers particularly many advantages. The oblique arrangement in the mask unit relates, in particular, to a main plane of the mask unit. The profile of a flow channel is, in particular, determined by its longitudinal axis.

In particular, the flow channel extends at an angle of between about 10° and 50°, and preferably between about 20° and 40°, in the mask unit. Larger or smaller angles are also possible. An angle of 0° is also possible. In particular, the flow channels are arranged with respect to one another at an angle of between about 20° and 100°, and preferably between about 40° and 80°. Larger or smaller angles are also possible. An angle of 0°, i.e. a parallel arrangement of at least two flow channels, is also possible. At least two of the flow channels in particular do not extend parallel to one another.

In all configurations, it is possible for at least one flow channel at least in sections to be bent and/or extend in the manner of a curve and/or at an angle. For example, the flow channel may be angled at about 90°+/−10°. Other angles are also possible. It is also possible for at least one of the flow channels to extend in a straight line at least in sections. For example, such a flow channel is cylindrical or cuboid or provided with a different geometry. In particular, the angled section provides at least one flow subchannel or is configured as such.

In one advantageous configuration, the flow channels are inclined at an angle of between about 10° and 50° with respect to a common symmetry axis, so that an emission direction toward an edge region of the mask unit is formed. It is also possible for there to be an emission direction in another direction. This offers particularly advantageous discharge of the exhaled air. In particular, the flow channels are inclined at an angle of between about 10° and 50°, and preferably at an angle of between about 20° and 40°, with respect to the common symmetry axis. Larger or smaller angles are also possible. An arrangement of the flow channels at an angle of 0°, i.e. without inclination, is also possible. The symmetry axis is, in particular, a rotational symmetry axis.

The flow channels are preferably arranged annularly on the mask unit. Preferably, the longitudinal axes of the flow channels intersect at a common point. In particular, the flow channels are in this case arranged in such a way that a screen-shaped distribution of the emission directions is formed, which is preferably directed toward an outer side of the mask unit. This offers many advantages in the discharge of the exhaled air. In particular, a common axis, and for example a symmetry axis with respect to which the flow channels are inclined at an angle, and preferably at the angle described above, extends through the common point. The flow channels may be spaced apart uniformly or nonuniformly from one another in the annular arrangement.

Preferably, the flow channels are arranged annularly around the connection unit in the mask body. Preferably, the flow channels are arranged circularly on the mask unit. In particular, the flow channels are arranged on a circular path. The flow channels may be arranged rotationally symmetrically. The annular arrangement may be configured in the manner of a rectangle or triangle or of an oval. A different arrangement of the flow channels on the mask unit is also possible.

It is preferred for the flow channels to be distributed uniformly over at least one subsection of the annular arrangement. Preferably, the flow channels are omitted, or closed, over at least one other subsection of the annular arrangement. Thus, an undesired flow impinging on facial regions may be influenced in a particularly controlled way. In particular, the other subsection is directed toward the eyes during intended use of the respiratory mask. Other orientations are also possible. In particular, the flow channels have emission directions which are directed away from the eyes.

In one preferred configuration, at least one of the flow channels comprises an outlet opening which is arranged transversely with respect to an inlet opening. In particular, a flow of the exhaled gas is thereby diverted before emerging from the respiratory mask. This configuration also offers many advantages. In particular, the outlet opening is arranged at an angle of between about 60° and 120°, and preferably between about 80° and 100°, with respect to the inlet opening. For example, the outlet opening is arranged at an angle of about 90° with respect to the inlet opening. In this and other configurations, provision may be made for the angles indicated, particularly the angle of about 90°, to deviate by up to 5° or more upward or downward.

In all configurations, it is particularly preferred for the flow subchannels to be produced by at least one casting process. In this way, the above-described flow subchannels, or the flow channels, may be produced particularly economically and at the same time reliably. Particularly preferably, the emission device is produced by at least one casting process. It is also preferred for the mask unit, and in particular the mask body and/or the connection unit, to be produced by at least one casting process. The emission device and the mask unit may be produced in a common casting process. Separate casting processes are also possible. An injection-molding process is preferably provided. In particular, the and/or other parts of the respiratory mask are produced by injection molding. Other casting processes are also possible.

Particularly preferably, the parts produced in the casting process are made of plastic, and preferably of at least one thermoplastic. At least one thermoset and/or at least one elastomer or the like may also be provided. Other plastics or materials are also possible.

In particular, the flow subchannel is produced by casting into at least two mutually complementary casting tools, each having at least one projection protruding at least partially into at least one common flow channel during the casting. The flow subchannel may be produced by casting into at least one casting tool having at least one retractable projection which protrudes at least partially into at least one flow channel during the casting. A flow subchannel produced in such a way may be provided economically and allows particularly advantageous configurations of the emission device. The projections of the mutually complementary casting tools in particular protrude into the same flow channel. In particular, the at least two projections complement one another to form a geometry of the flow channel. The projection may, for example, be configured in the shape of a cone or in the shape of a rod. Other geometries are also possible.

It is possible for the emission device to be provided by at least one cast part. Preferably, the cast part is connected to the mask unit by injection-overmolding and/or by overcasting. In particular, the cast part is connected to the mask body and/or to the connection unit in such a way. The cast part may be connected to the mask unit by another process. For example, the cast part may be welded and/or adhesively bonded to the mask unit. In particular, the cast part is connected integrally to the mask unit. Such stepwise production offers many advantages.

The emission device is, in particular, produced by at least one casting process and connected to the mask unit by at least one further casting process. The mask unit is, in particular, produced in the further casting process. It is, however, also possible and preferred for the mask unit, in particular the mask body and/or the connection unit, to be produced together with the emission device in one casting process.

In all configurations, it is preferred for the flow channels to be arranged in the mask body and/or in the connection unit. This offers particularly advantageous fitting of the flow channels. It is possible for all flow channels to be arranged in the mask body or in the connection unit. It is also possible for some of the flow channels to be arranged in the mask body and others to be arranged in the connection unit. In particular, a flow channel is in each case arranged either fully in the mask body or fully in the connection unit. In particular, a flow channel is in each case delimited either by the mask body or by the connection unit.

According to the invention, the flow channels are arranged in the emission device. The emission device may be a part (region) of the mask body and to this extent be integral (with the mask body). The emission device may be a separate component, which is connected to the mask body with a form, material or force fit.

As an alternative or in addition, the emission device may also be a part (region) of the connection unit and to this extent be integral (with the connection unit). The emission device may be a separate component, which is connected to the connection unit with a form, material or force fit.

It is, however, also possible for at least one of the flow channels to be arranged partially in the mask body and partially in the connection unit. Then, the flow channel is in particular bounded by the mask body and the connection unit.

The emission device may be manufactured as a separate part and then injection-molded onto the mask body (two-component process).

The emission device may be manufactured as a separate part which is then pressed into a corresponding undercut in the mask body. This has the advantage that the fine precision part is manufactured separately in an optimized process.

The aim of all embodiments is to achieve a flow direction which is directed in the form of a screen outward, for example at an angle of about 10°-50° away from the face. The outlet opening of all embodiments is therefore directed at an angle outward. The flow is directed forward away from the face. The exit angle is therefore, for example, to be oriented excessively radially. It is also conceivable to give the flow channels different emission directions and thus to spread the flow even further. In this way, the flow energy is distributed over a larger region, which leads to less sound emission.

The process according to the invention is used for producing a respiratory mask, in particular for a respirator apparatus, and preferably for a sleep therapy apparatus. The respiratory mask produced comprises at least one mask unit and at least one emission device for discharging exhaled gas from the respiratory mask. The mask unit comprises at least one mask body and at least one connection unit which can be connected to the mask body for connection of a respiratory gas feed line. The emission device is equipped with a multiplicity of flow channels. The flow channels are arranged in at least one part of the mask unit, and preferably in the mask body and/or in the connection unit. In this case, the emission device is produced by means of at least one casting process, in particular by means of injection molding, while being equipped with at least one flow subchannel.

The process according to the invention offers many advantages. For example, particularly economical production of the respiratory mask is possible, so that it can be provided to a large range of patients or users.

Preferably, the process is used for producing the respiratory mask according to the invention. In particular, the respiratory mask described above is produced by the process according to the invention. Particularly preferably, the flow channels are produced at least partially by means of the casting process while being equipped with at least one flow subchannel.

Preferably, the emission device is cast into at least two mutually complementary casting tools. Preferably, in this case at least one projection protrudes in each case from the casting tools at least partially into at least one common flow channel during the casting. It is also possible for the emission device to be cast into at least one casting tool. Preferably, in this case at least one projection protrudes at least partially into at least one flow channel during the casting. The projection is subsequently retracted and thereby removed at least partially from the flow channel.

The respiratory mask is in particular suitable and configured to be used for a sleep therapy apparatus. The respirator apparatus is, in particular, a sleep therapy apparatus. The connection unit is preferably equipped with a tube flange. In particular, the respiratory mask is intended for a single-tube system. The tube is in this case used for the supply with respiratory gas. In particular, no tube is provided for discharging the exhaled gas. In particular, the emission device is suitable and configured to discharge the exhaled gas directly from the respiratory mask into the surroundings. During intended use of the respiratory mask, the flow channels are, in particular, arranged in a region over the mouth and/or over the nose.

Preferably, the connection unit is releasably coupled to the mask body and, in particular, connected by means of at least one latching connection. In particular, the connection unit can be inserted into a connection opening of the mask body. The connection unit may be configured to be angled or straight. The connection unit may comprise at least one angle piece or be configured as such. The mask unit may comprise at least one forehead support and/or at least one mask plate. The forehead support is, in particular, fastened on the mask body or firmly connected thereto. The mask plate is, in particular, releasably connectable to the mask body.

In particular, at least one flow subchannel is suitable and configured to make it possible to take the emission device and/or at least a part of the mask unit from a casting mold with a form fit.

The above-described configurations of the at least one flow channel, or of the at least two flow channels, are preferably provided for all flow channels or for a majority of the flow channels.

Further advantages and features of the present invention may be found in the description of the exemplary embodiments, which will be explained below with reference to the appended figures.

DETAILED DESCRIPTION OF EXEMPLARY EMBODIMENTS

The particulars shown herein are by way of example and for purposes of illustrative discussion of the embodiments of the present invention only and are presented in the cause of providing what is believed to be the most useful and readily understood description of the principles and conceptual aspects of the present invention. In this regard, no attempt is made to show details of the present invention in more detail than is necessary for the fundamental understanding of the present invention, the description in combination with the drawings making apparent to those of skill in the art how the several forms of the present invention may be embodied in practice.

Figure 1:
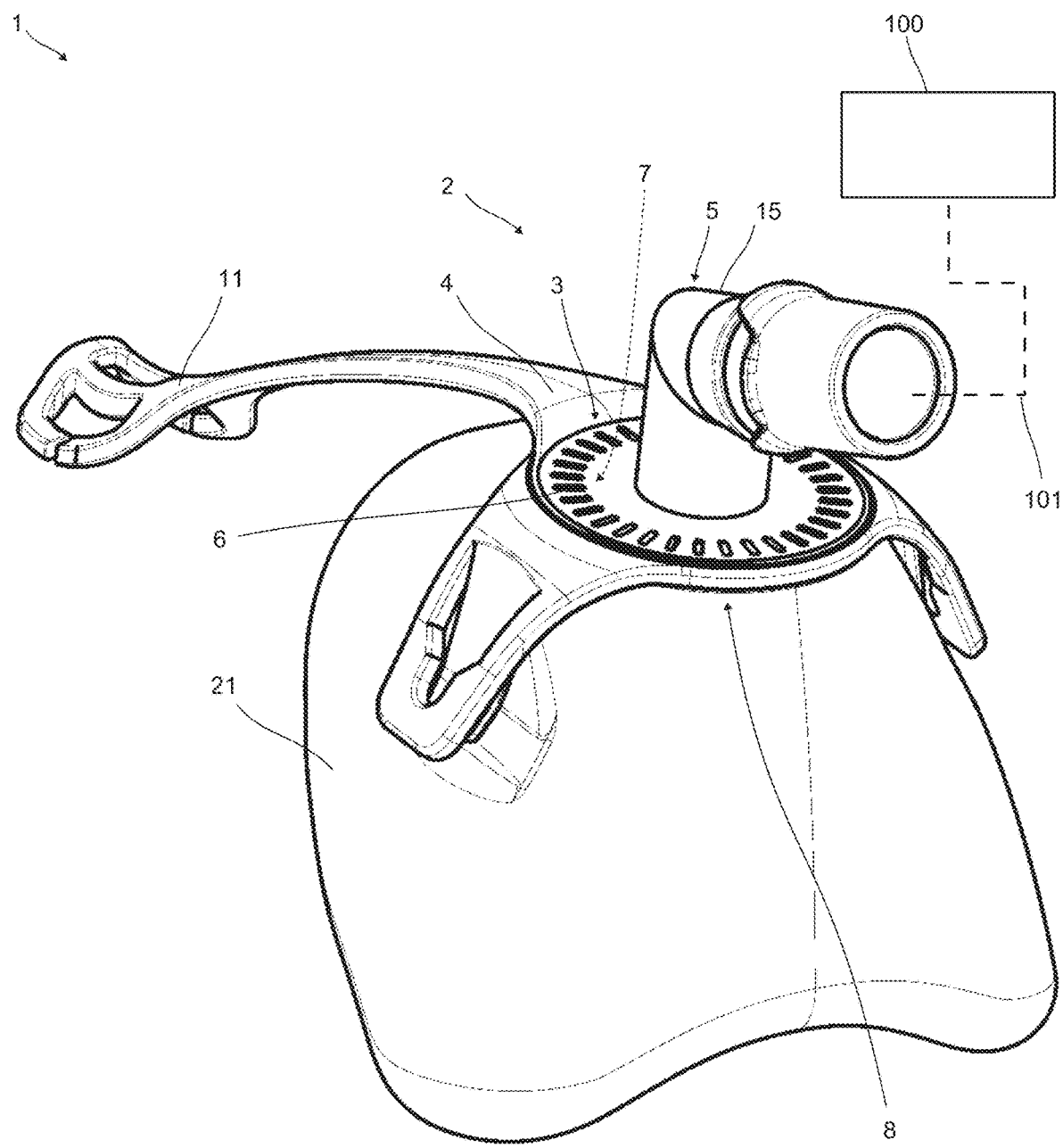
FIG. 1 shows a purely schematic representation of a respiratory mask according to the invention in a perspective view.

FIG. 1 shows a respiratory mask 1 according to the invention, which in this case is used with a respirator apparatus 100 configured as a sleep therapy apparatus. The respiratory mask 1 comprises a mask unit 2, which has a mask body 4 and a connection unit 5. A mask plate 21 is in this case fastened on the mask body. Furthermore, the mask body 4 is equipped with a forehead support 11.

The connection unit 5 is in this case inserted into a corresponding connection opening of the mask body 4 and, for example, latched. The connection unit 5 is in this case provided with an angle piece 15 and is used for the connection of a respiratory gas feed line 101, and for example of a respiratory tube, to the mask 1. The respiratory tube is in this case connected to the respirator apparatus 100.

In order to be able to discharge the exhaled air from the mask 1 an emission device 3 having a multiplicity of flow channels is provided. The exhaled air is released into the surroundings through the flow channels 6. The emission device 3 is in this case part of the mask body 4. To this end, the flow channels 6 flow through the mask body 4. In addition or as an alternative, the flow channels 6 may also be provided in the connection unit 5.

The flow channels 6 in this case have a rectangular cross-sectional profile with rounded corners, and are arranged annularly around the connection unit 5 on the mask body 4. In this case, the flow channels 6 are distributed uniformly. In one configuration (not shown here) a subsection of the annular arrangement may be configured with closed flow channels 6 or even without flow channels 6. Such a subsection is, for example, directed toward the eyes or is arranged below the forehead support 11.

Figure 27:
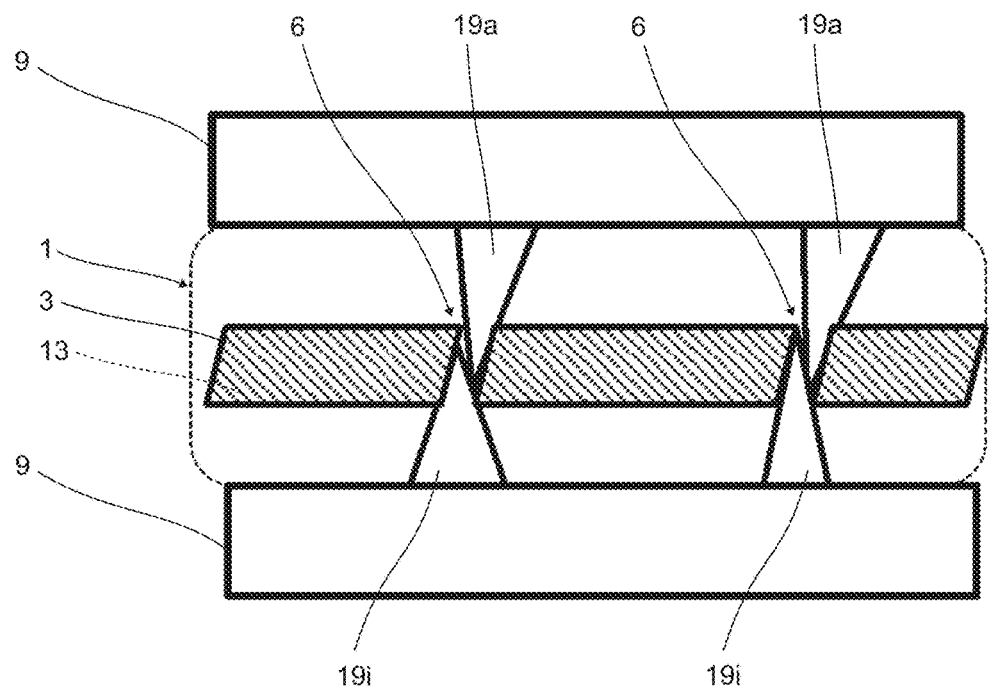
FIG. 27 shows a purely schematic representation of production of a respiratory mask by the process according to the invention.
Figure 28:
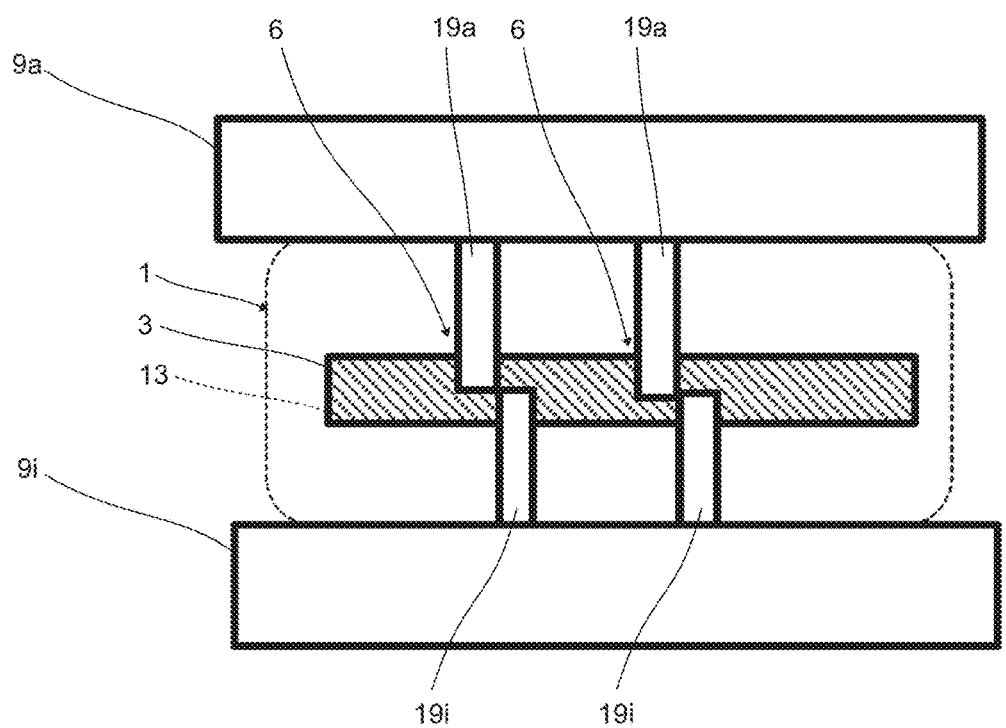
FIG. 28 shows a purely schematic representation of production of a respiratory mask by the process according to the invention.

The emission device 3 is produced in a casting process and, for example, by injection molding. During production, the emission device 3 is provided with a flow subchannel 7 (not visible in the representation shown here). In order to be able to remove the emission device 3 from a casting mold in spite of the flow subchannel 7, or in order to avoid form-fit blocking of the removal, the process according to the invention described in more detail with reference to FIGS. 27 and 28 is used.

Figure 2:
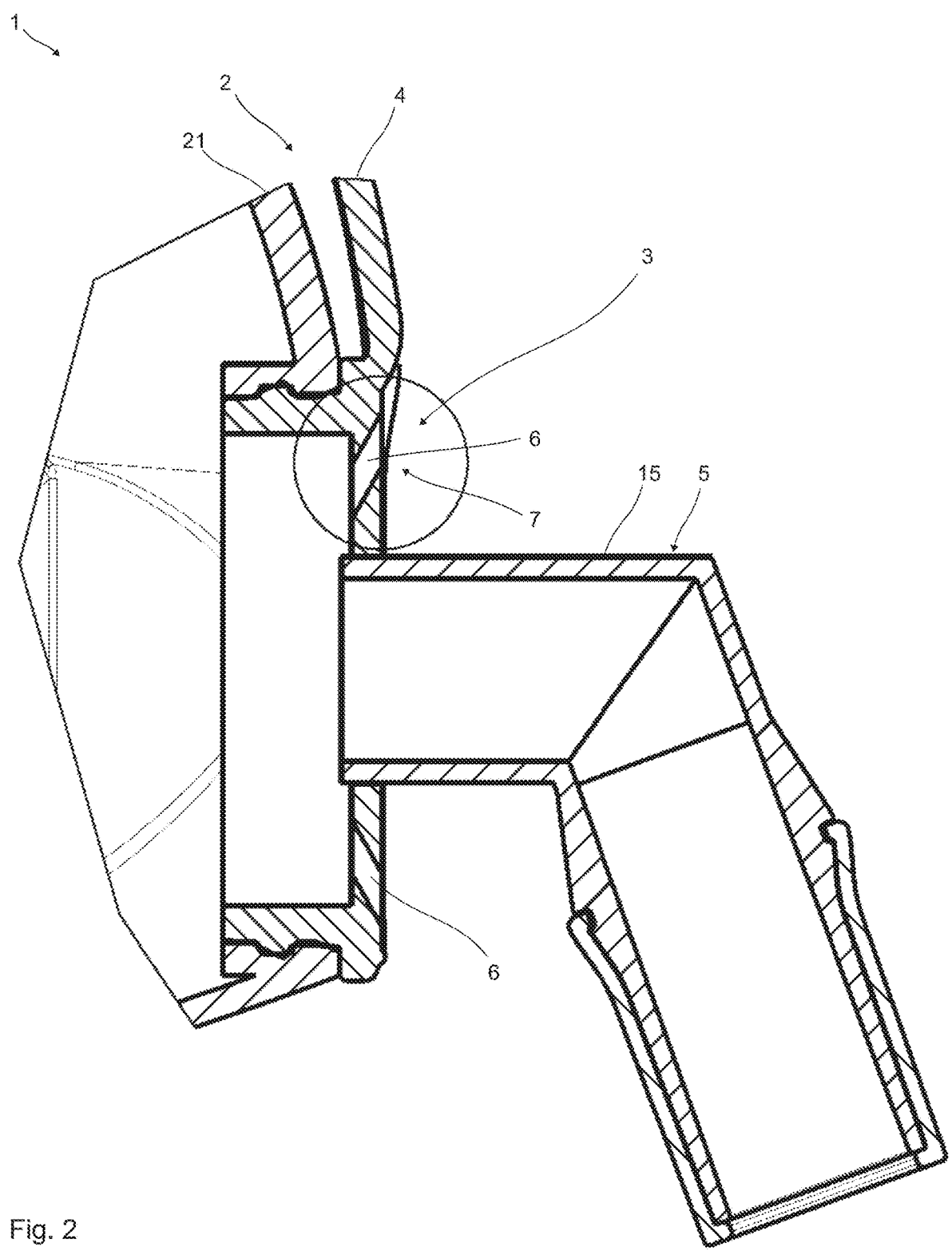
FIG. 2 shows the respiratory mask of FIG. 1 in a sectional side view.

FIG. 2 shows a sectional detail view of the respiratory mask 1, which represents in more detail the region of the emission device 3. The configuration of the flow channels 6 can be seen particularly well in this case.

The flow channels are provided here with a constant, or steady, channel cross section. The flow channels 6 in this case extend obliquely in the mask body 4 and also obliquely with respect to one another. For example, the flow channels 6 are in this case inclined at an angle of between about 20° and 40° with respect to a common symmetry axis. The longitudinal axes of the flow channels 6 in this case intersect at a common point. The exhaled air is thus discharged toward an edge region of the respiratory mask 1.

Figure 3:
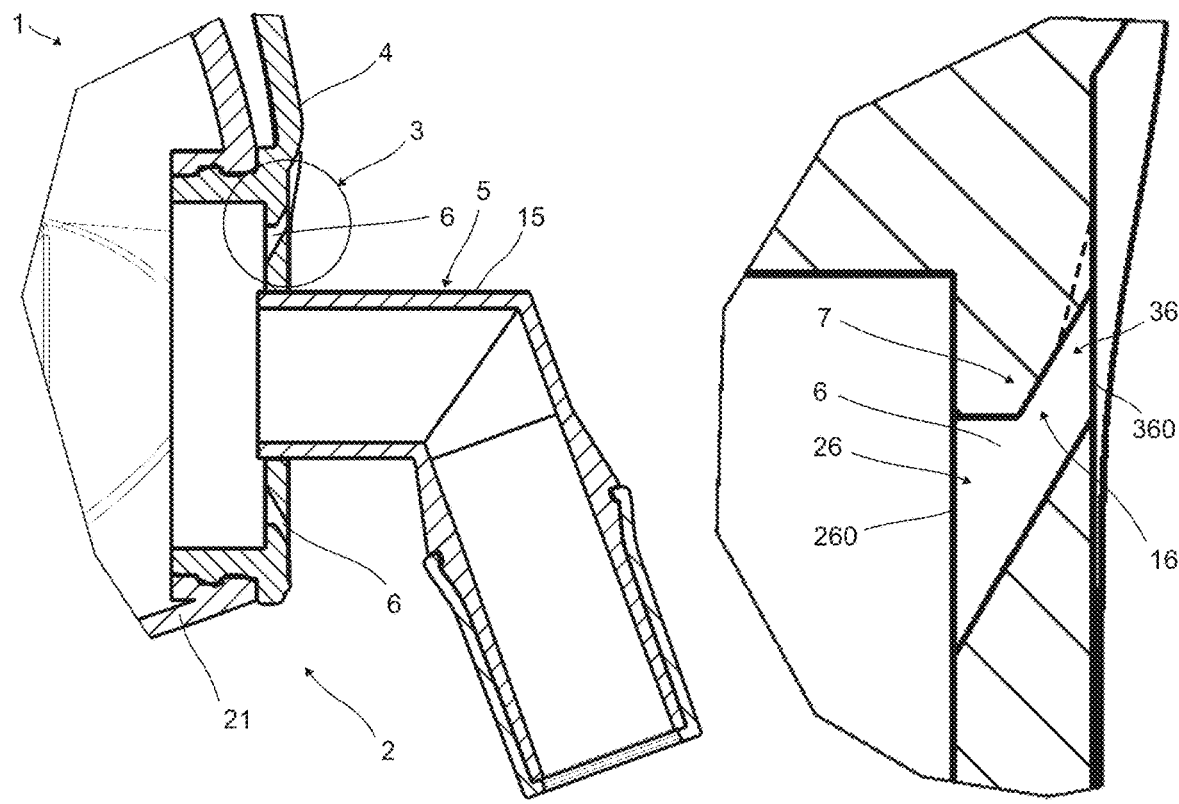
FIG. 3 shows a respiratory mask in a sectional side view with an enlarged detail view.

FIG. 3 shows a respiratory mask 1 having a different advantageous configuration of the emission device 3. The circularly bordered region of the emission device 3 is represented on an enlarged scale on the right in the image for better clarity.

The flow channels 6 are in this case provided in sections with a varying channel cross section. In the region of the varying channel cross section, the flow channels 6 are for example configured conically or in the shape of a cone.

A constriction section 16 is in this case respectively arranged in the flow channels 6. As can be seen particularly well in the enlarged detail representation, the constriction section 16 is in this case configured elongatedly. The flow channel 6 shown in this case extends between an inlet opening 260 and an outlet opening 360. Here, the inlet opening 260 is followed by an inlet region 26 which narrows in the shape of a funnel and extends as far as the constriction section 16. The constriction section 16 extends from there elongatedly as far as the outlet opening 360.

In a configuration shown by dashes here, the flow channel 6 may be equipped with an outlet region 36 which widens in the shape of a funnel and extends in the flow direction after the constriction section 16. In such a configuration, the exhaled air enters the inlet region 26 narrowing in the shape of a funnel and flows on from there through the distance of the constriction section 16 as far as the outlet region 36 widening in the shape of a funnel. There, the air enters the atmosphere through the outlet opening 360.

Figure 4:
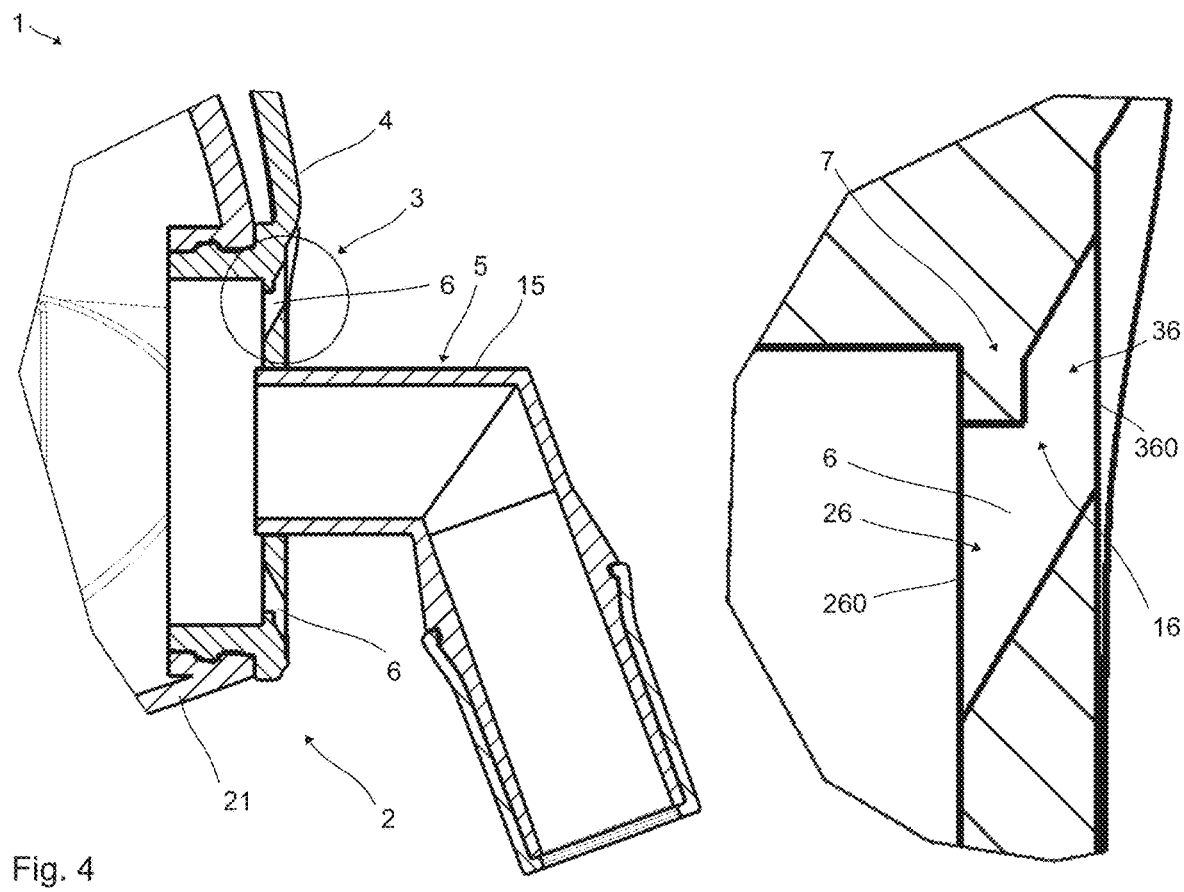
FIG. 4 shows a respiratory mask in a sectional side view with an enlarged detail view.

FIG. 4 shows a respiratory mask 1 having a different configuration of the emission device 3. The circularly bordered region is represented on an enlarged scale in the right-hand half of the image and shows an exemplary flow channel 6.

Arranged in the flow channel 6, there is in this case a shoulder which forms a constriction section 16 or is part of such. The inlet region 26 in this case narrows increasingly as far as the constriction section 16. After the constriction section 16, the flow channel 6 widens again.

Figure 5:
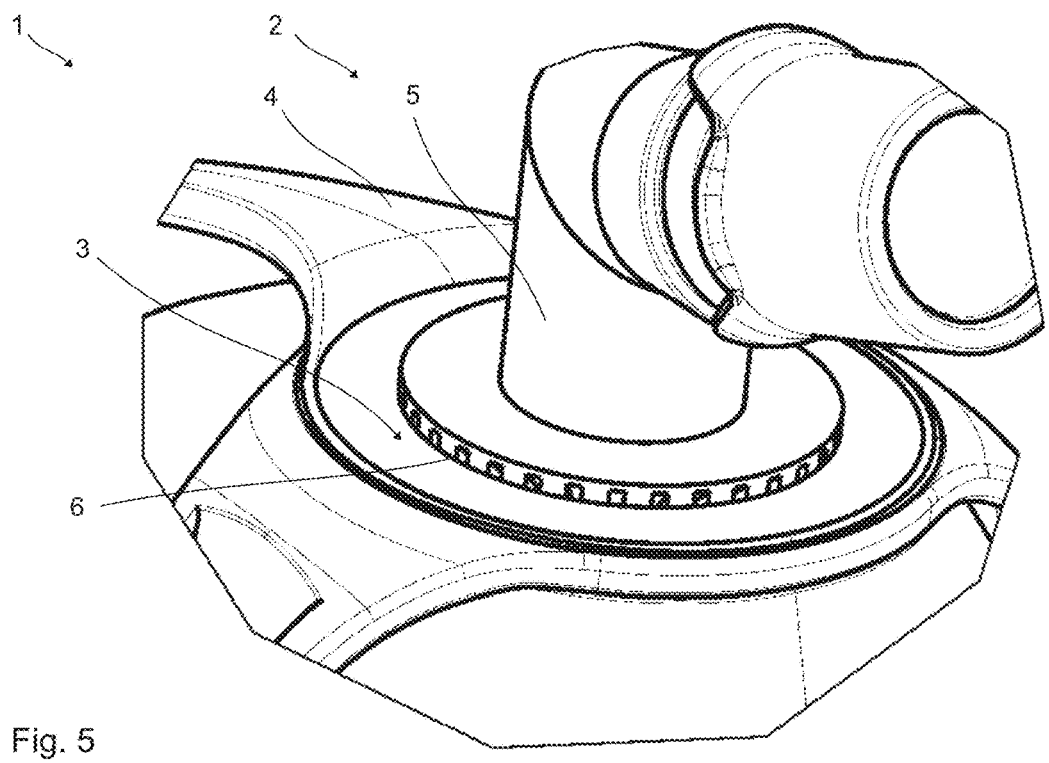
FIG. 5 shows a respiratory mask in a perspective detail view.
Figure 6:
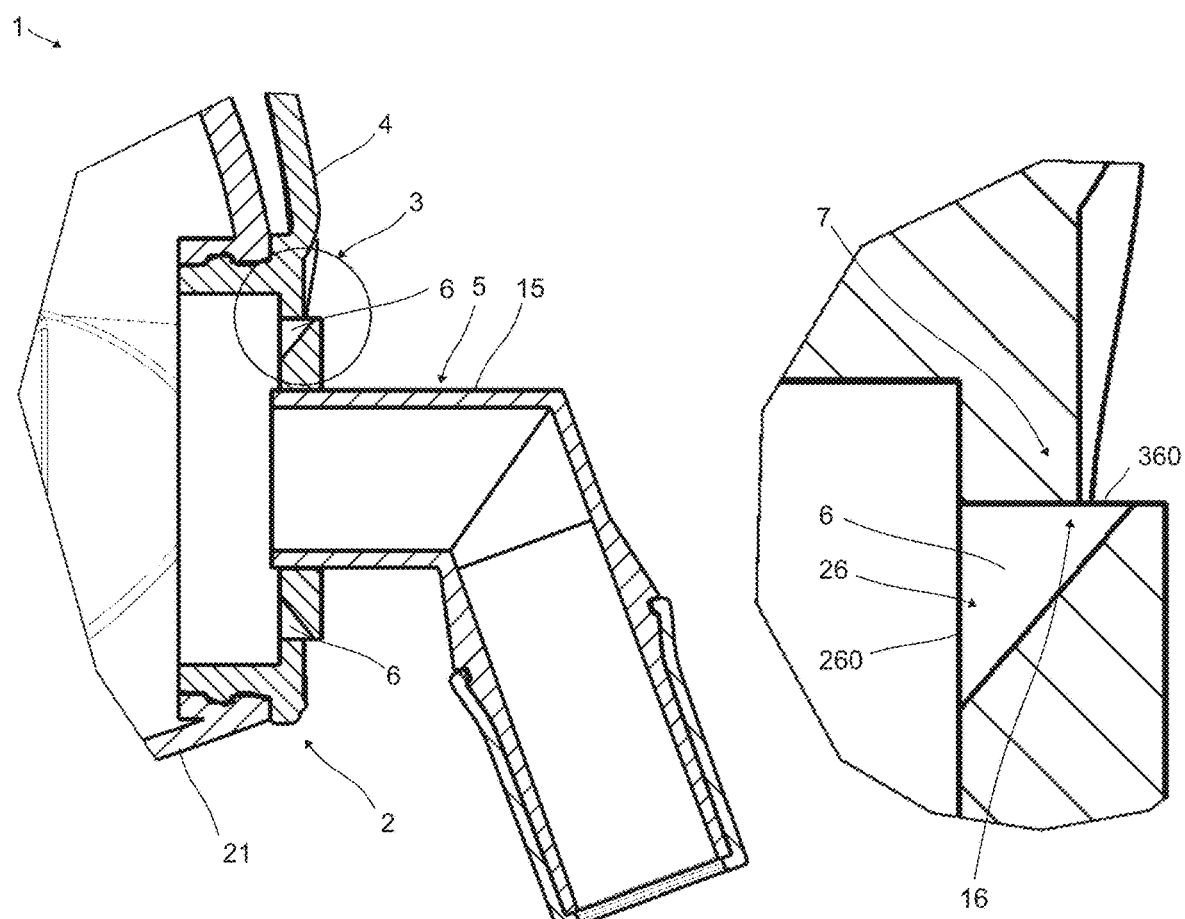
FIG. 6 shows the respiratory mask of FIG. 5 in a sectional side view with an enlarged detail view.

FIG. 5 shows an excerpt of one configuration of the respiratory mask 1 according to the invention. FIG. 6 in this case shows a sectional detail representation of FIG. 5, the circularly bordered region being represented on an enlarged scale in the right-hand half of the image. The flow channels in this case comprise outlet openings 360, which are arranged transversely to the respective inlet openings 260. The outlet openings 360 are arranged at an angle of about 70-120°, preferably about 90°, to the respective inlet openings 260. The flow of the exhaled air is thus diverted before emerging from the respiratory mask 1. The inlet opening 260 comprises a funnel-like region, which tapers to a constriction 16 and then merges into the outlet opening 360. At least one subregion of the outlet opening 360 lies above a plane E which is defined by the mask body 4. Next to the outlet opening 360, the mask body comprises a subregion which is chamfered and is used as a flow guide surface.

Figure 7:
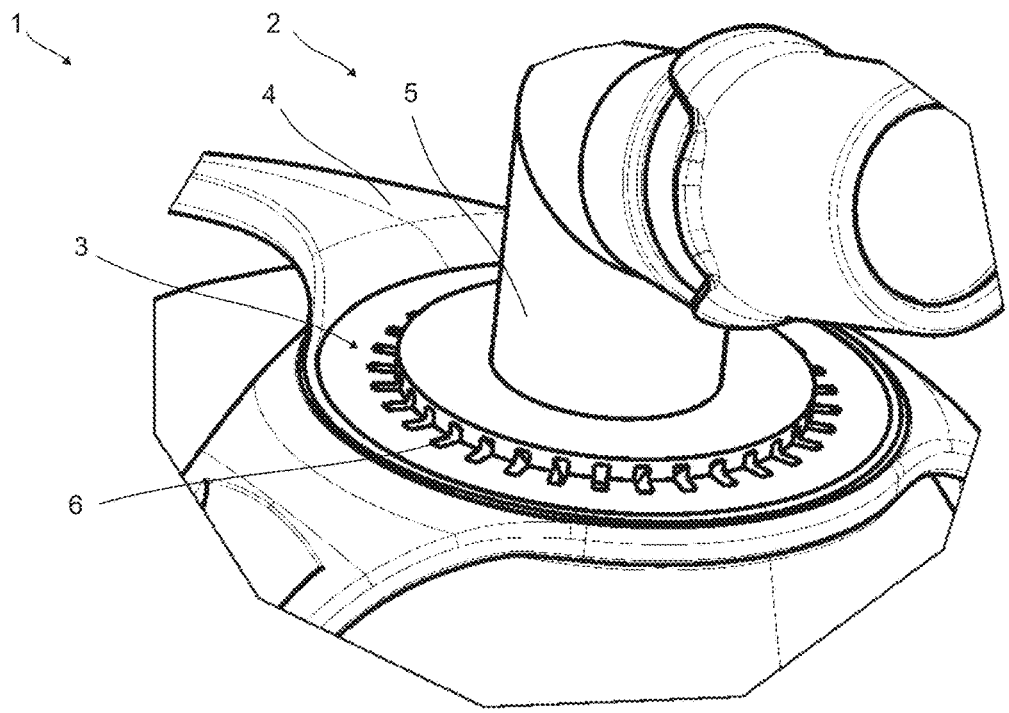
FIG. 7 shows a respiratory mask in a perspective detail view.
Figure 8:
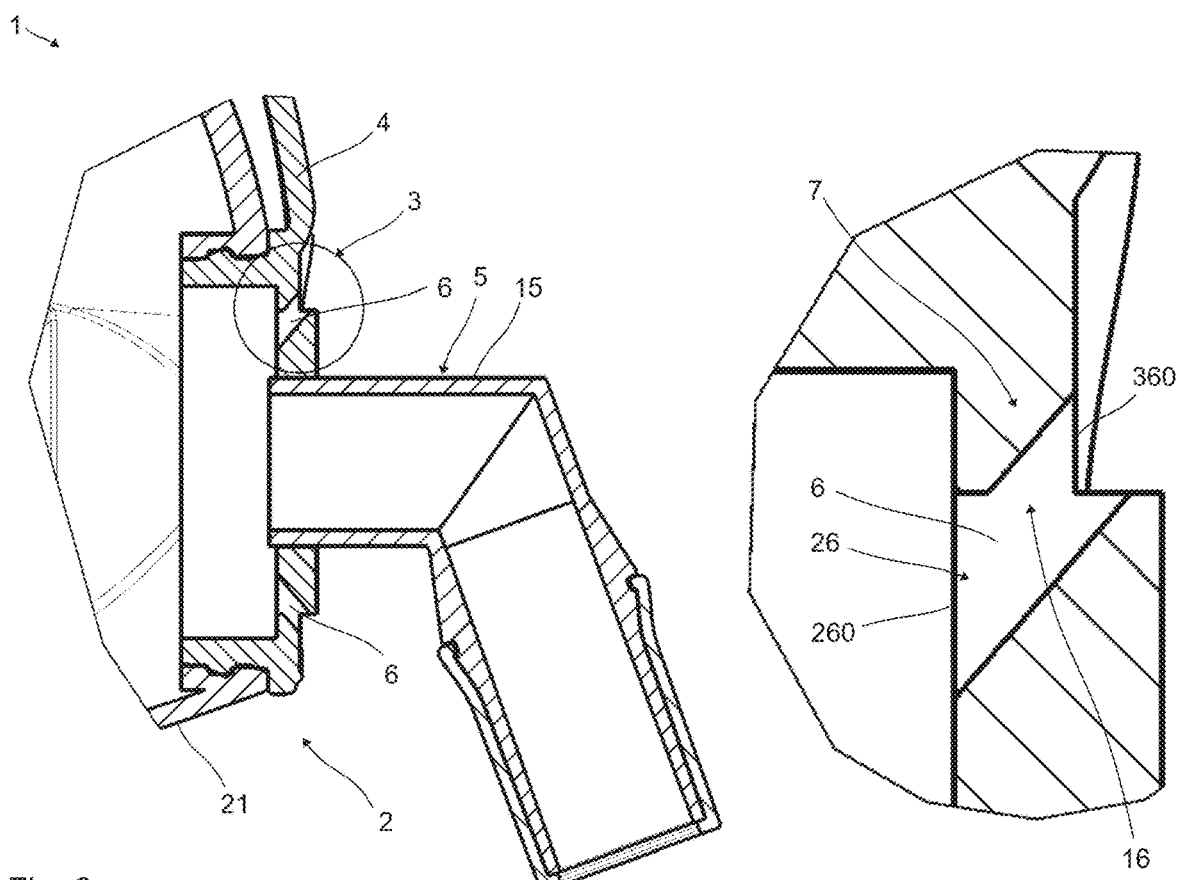
FIG. 8 shows the respiratory mask of FIG. 7 in a sectional side view with an enlarged detail view.
Figure 9:
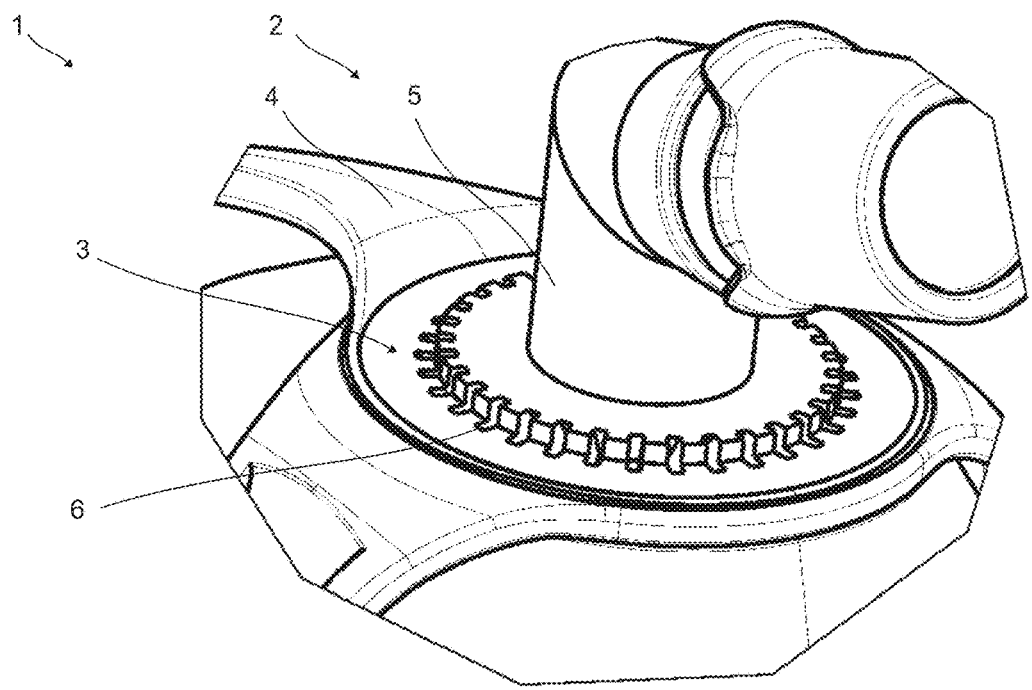
FIG. 9 shows a respiratory mask in a perspective detail view.
Figure 10:
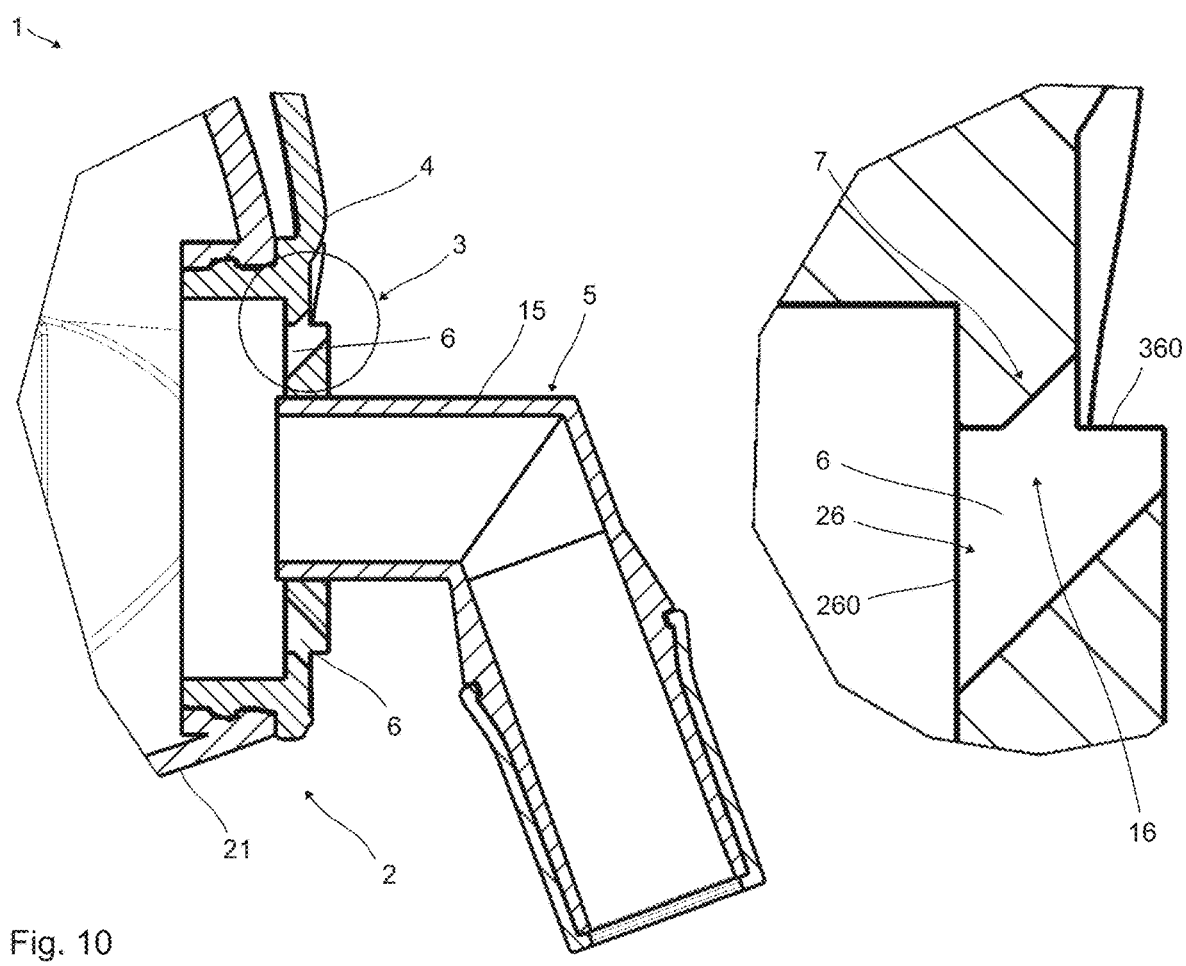
FIG. 10 shows the respiratory mask of FIG. 9 in a sectional side view with an enlarged detail view.
Figure 11:
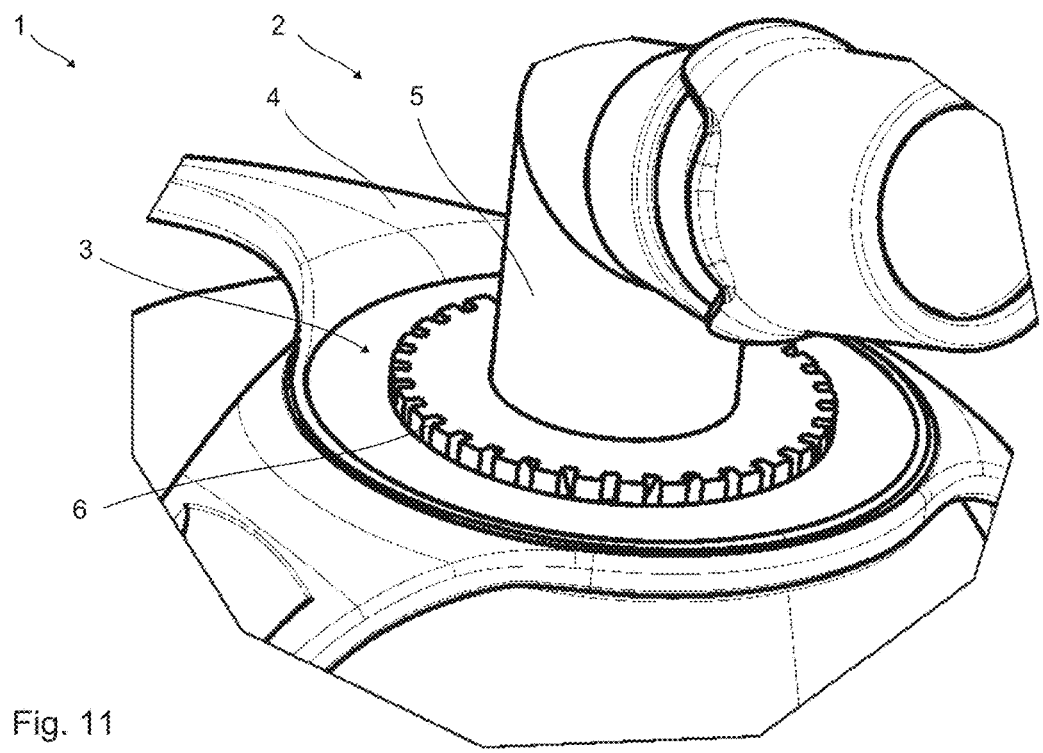
FIG. 11 shows a respiratory mask in a perspective detail view.
Figure 12:
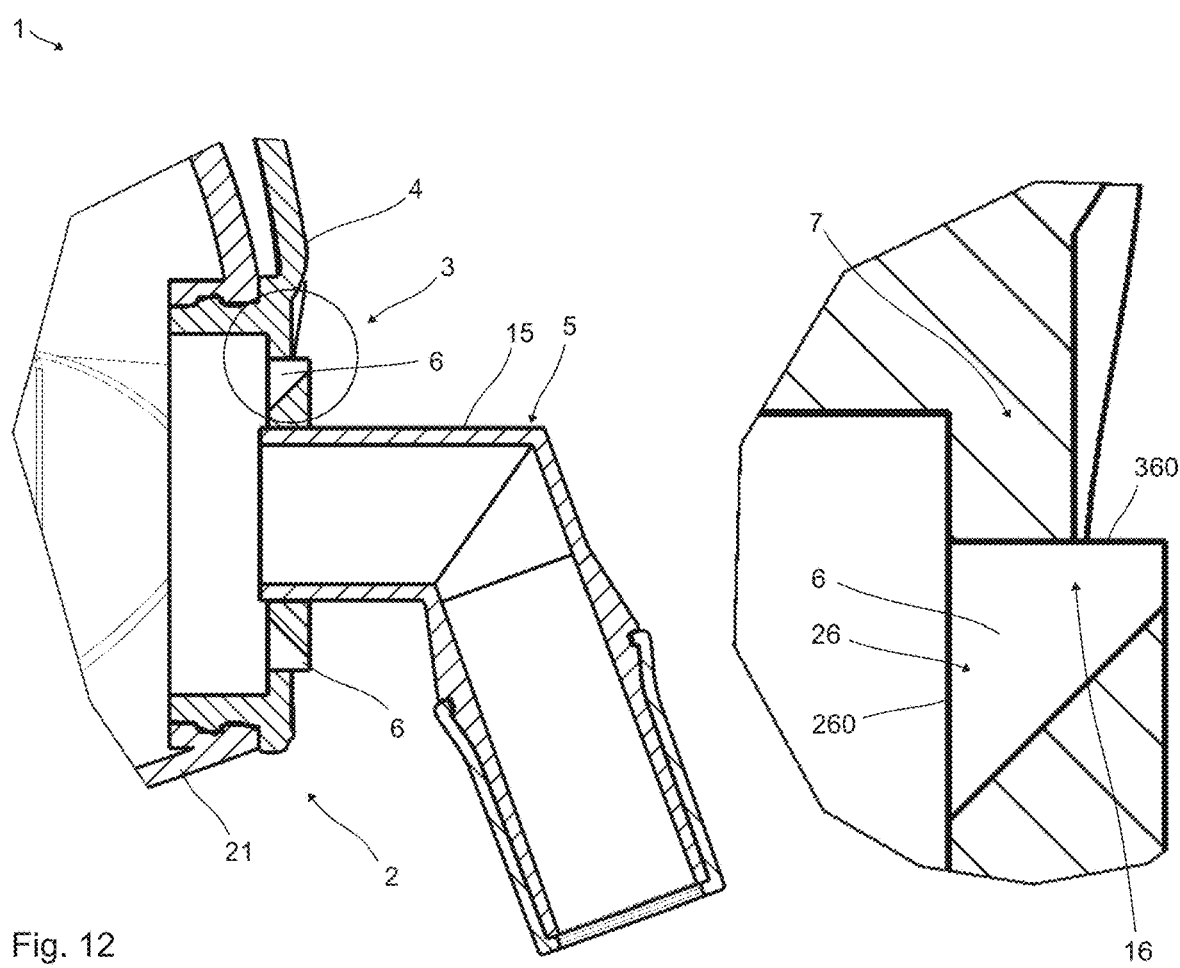
FIG. 12 shows the respiratory mask of FIG. 11 in a sectional side view with an enlarged detail view.
Figure 13:
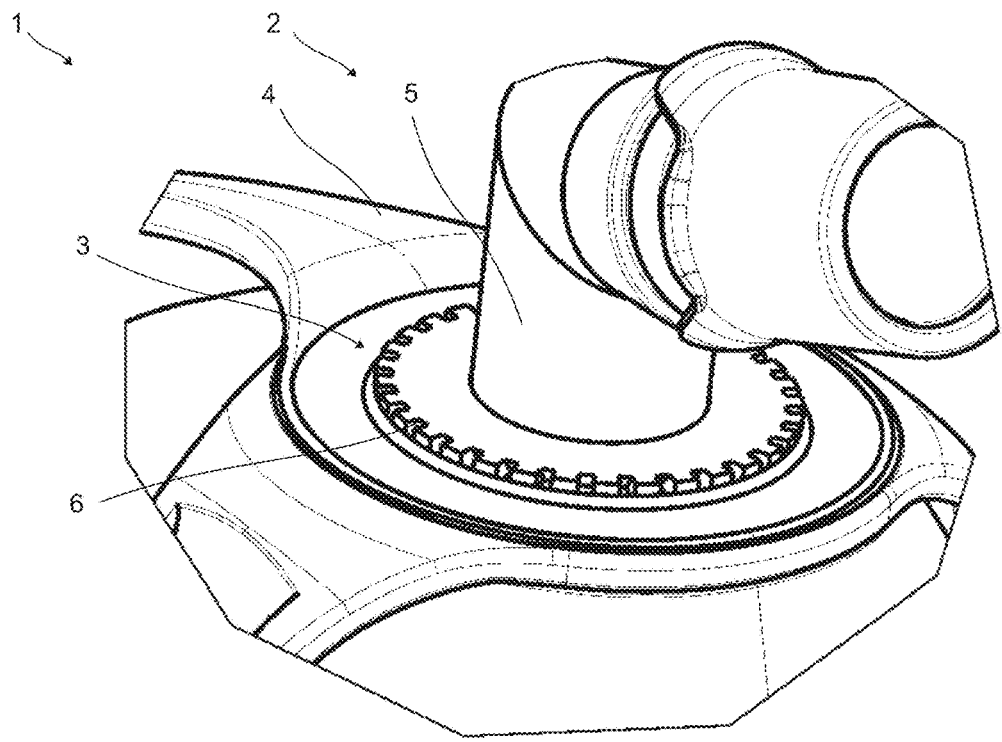
FIG. 13 shows a respiratory mask in a perspective detail view.
Figure 14:
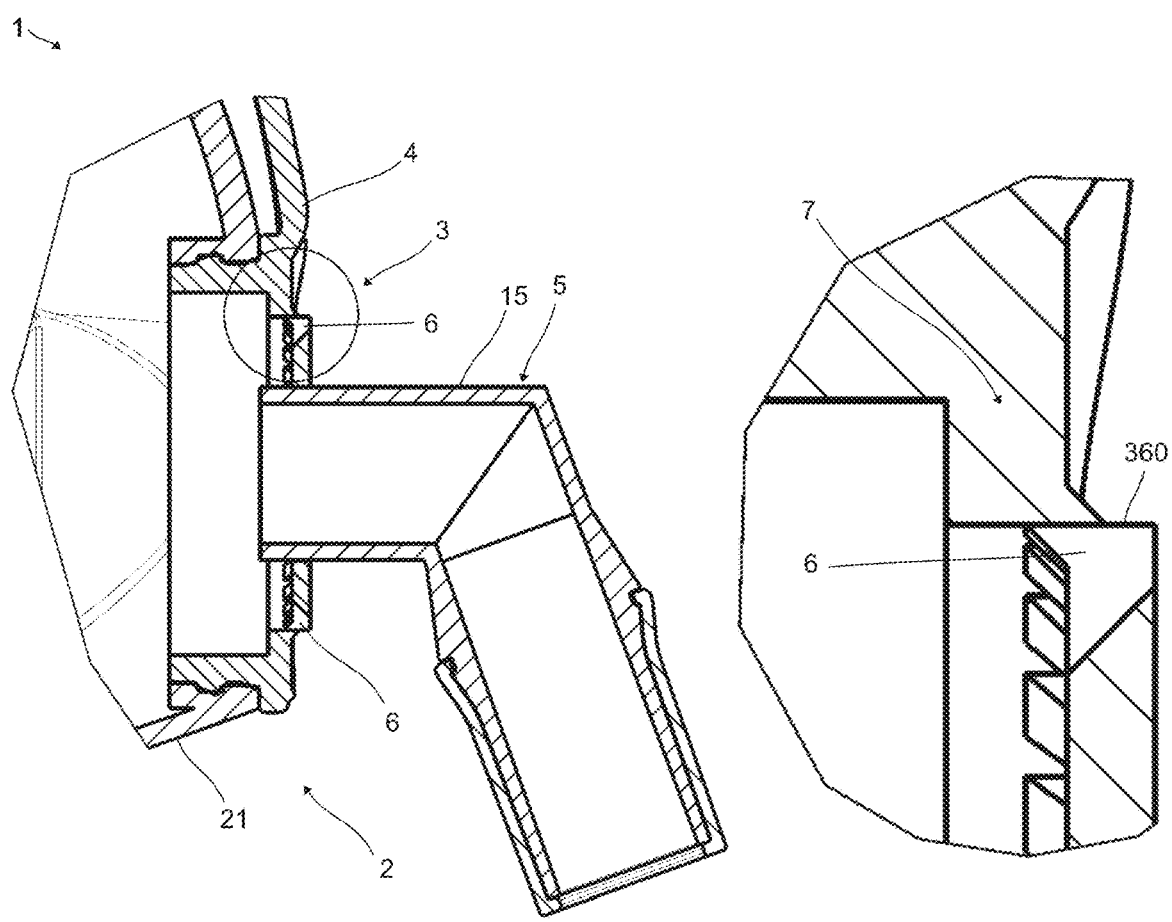
FIG. 14 shows the respiratory mask of FIG. 13 in a sectional side view with an enlarged detail view.
Figure 15:
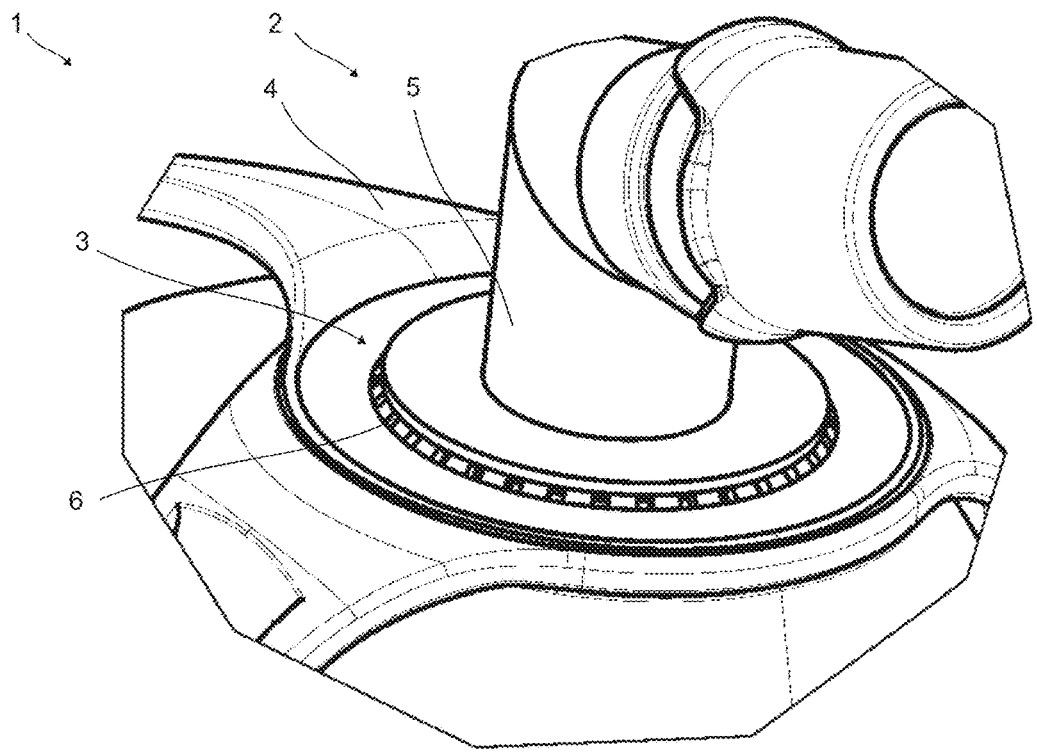
FIG. 15 shows a respiratory mask in a perspective detail view.
Figure 16:
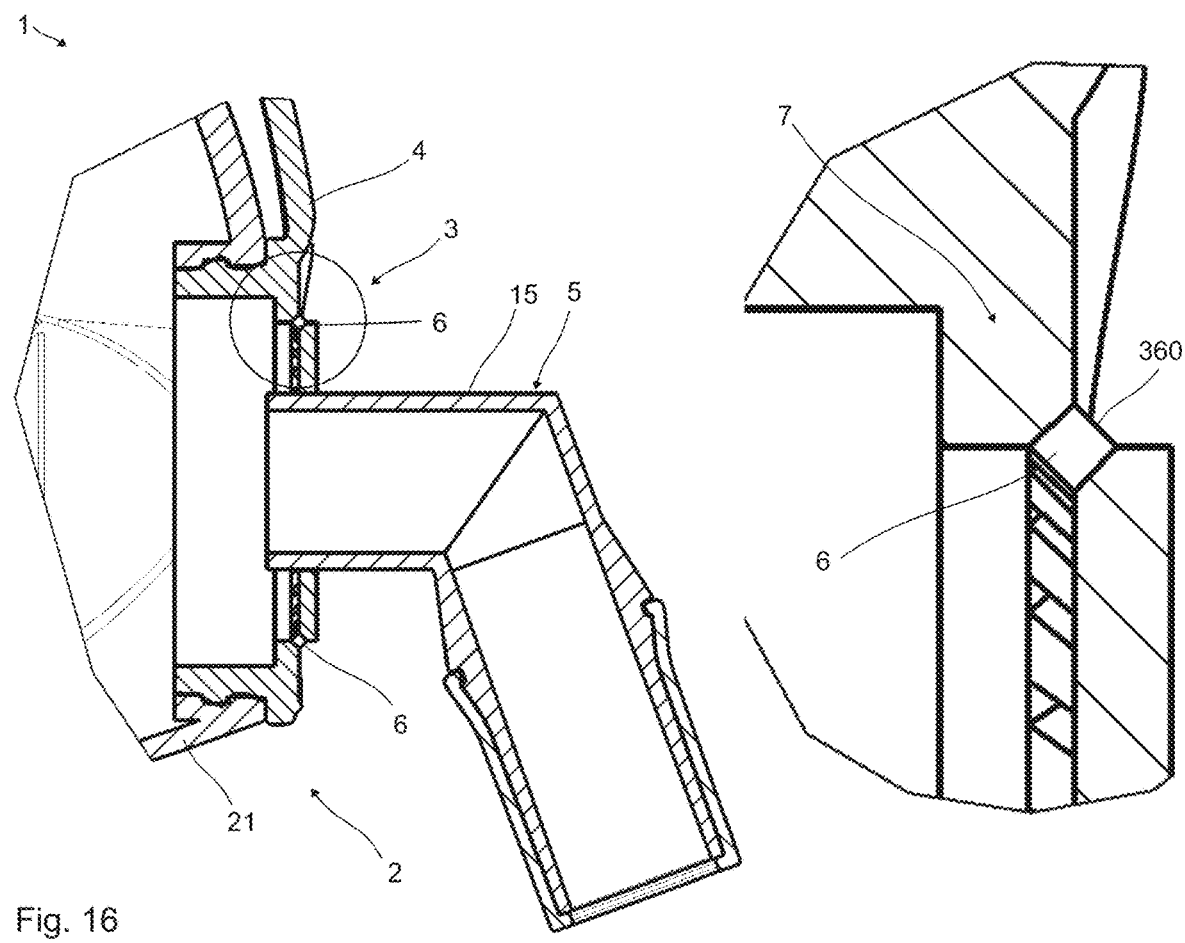
FIG. 16 shows the respiratory mask of FIG. 15 in a sectional side view with an enlarged detail view.
Figure 17:
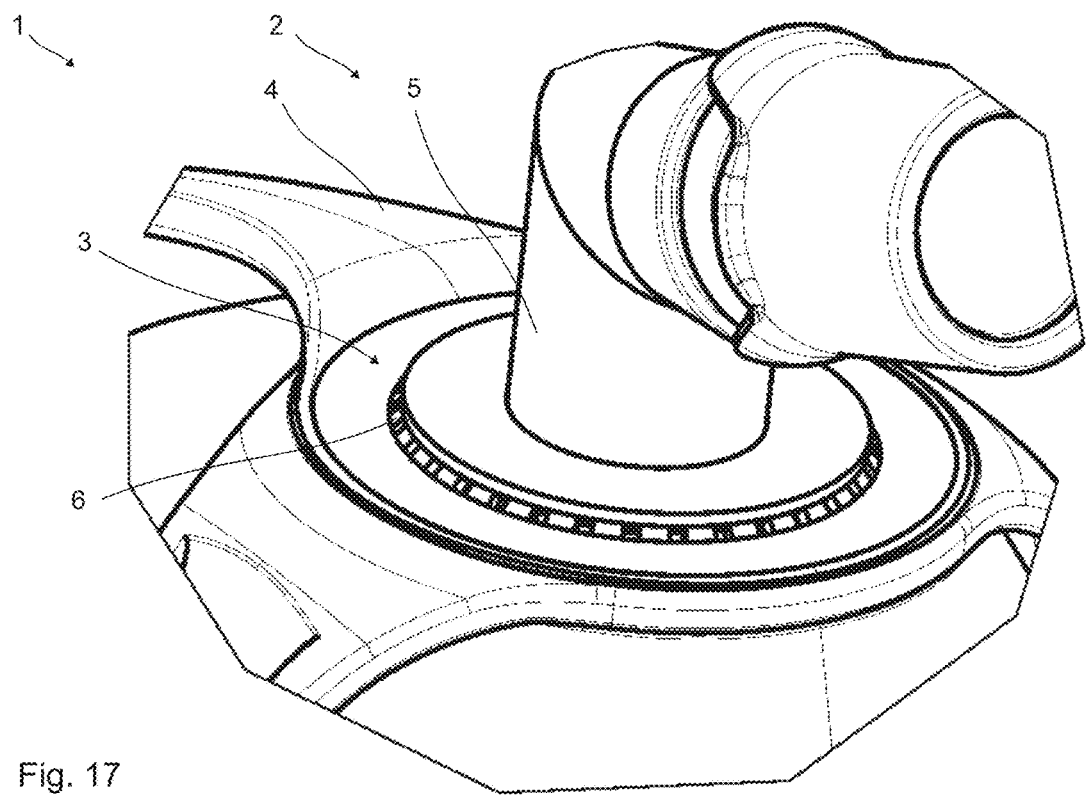
FIG. 17 shows a respiratory mask in a perspective detail view.
Figure 18:
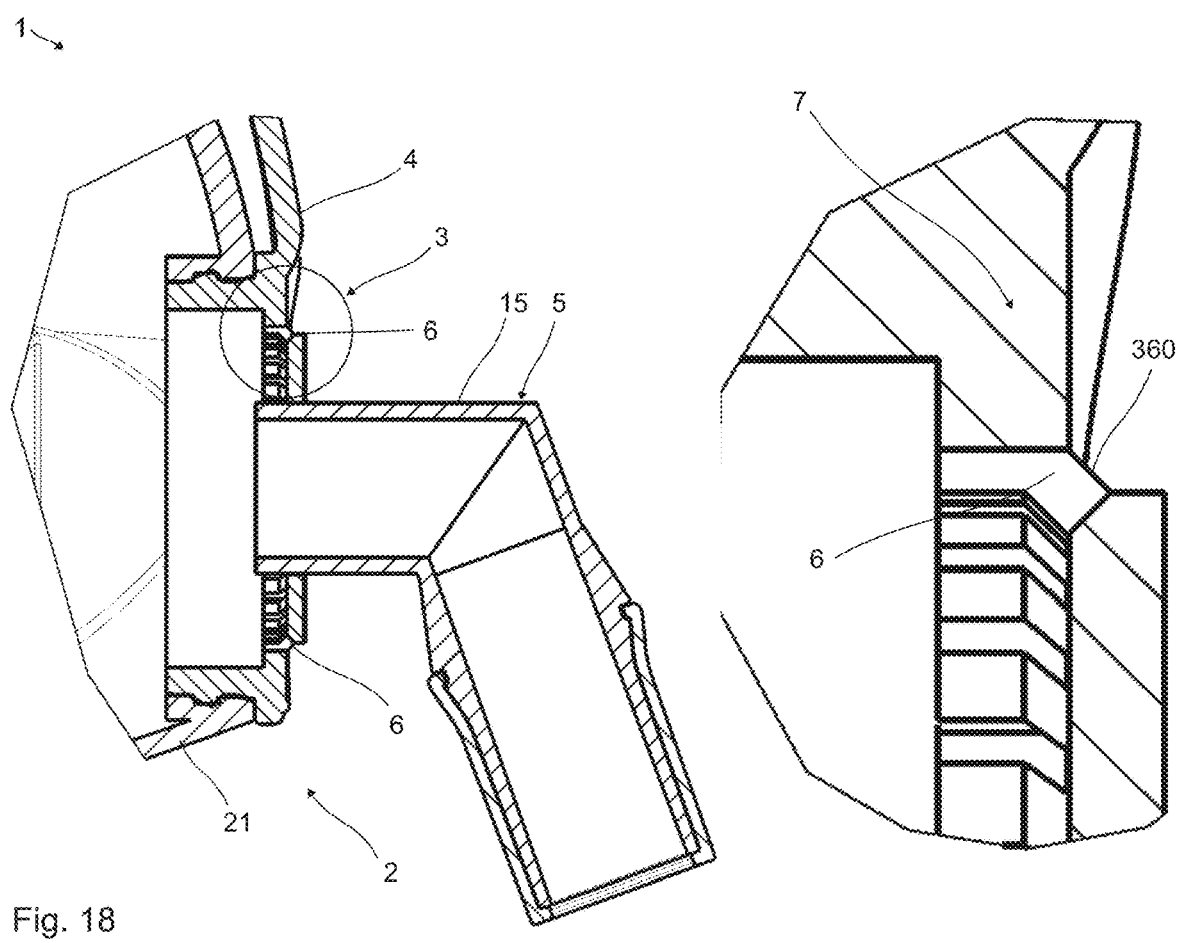
FIG. 18 shows the respiratory mask of FIG. 17 in a sectional side view with an enlarged detail view.

FIG. 7 shows one configuration of the respiratory mask 1 according to the invention. FIG. 8 in this case shows a sectional detail representation of FIG. 7, the circularly bordered region being represented on an enlarged scale in the right-hand half of the image. In this case, only a part of the outlet opening 360 is respectively arranged transversely to the respective inlet openings 260. In this way, a particularly advantageous flow behavior is achieved.

FIGS. 9, 11, 13, 15, 17 and 19 respectively show one configuration of the respiratory mask 1 according to the invention. FIGS. 10, 12, 14, 16, 18 and 20 in this case respectively show a sectional detail representation of the respectively preceding figure, the circularly bordered region being represented on an enlarged scale in the right-hand half of the image.

Figure 19:
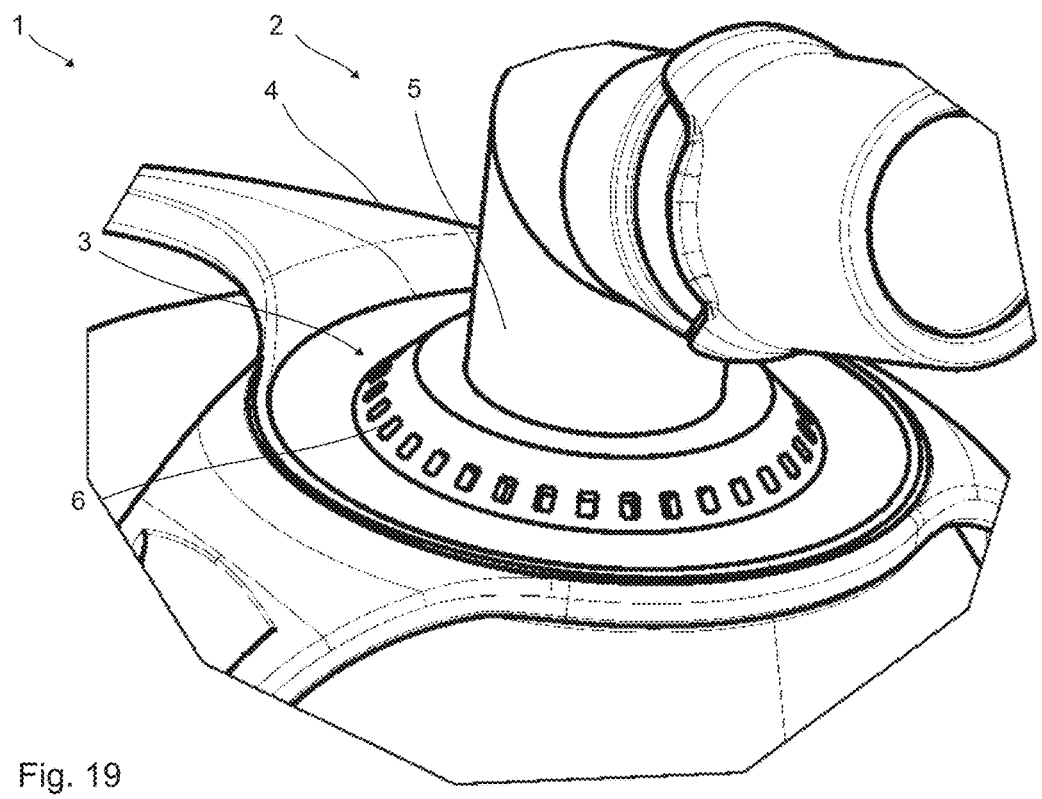
FIG. 19 shows a respiratory mask in a perspective detail view.
Figure 20:
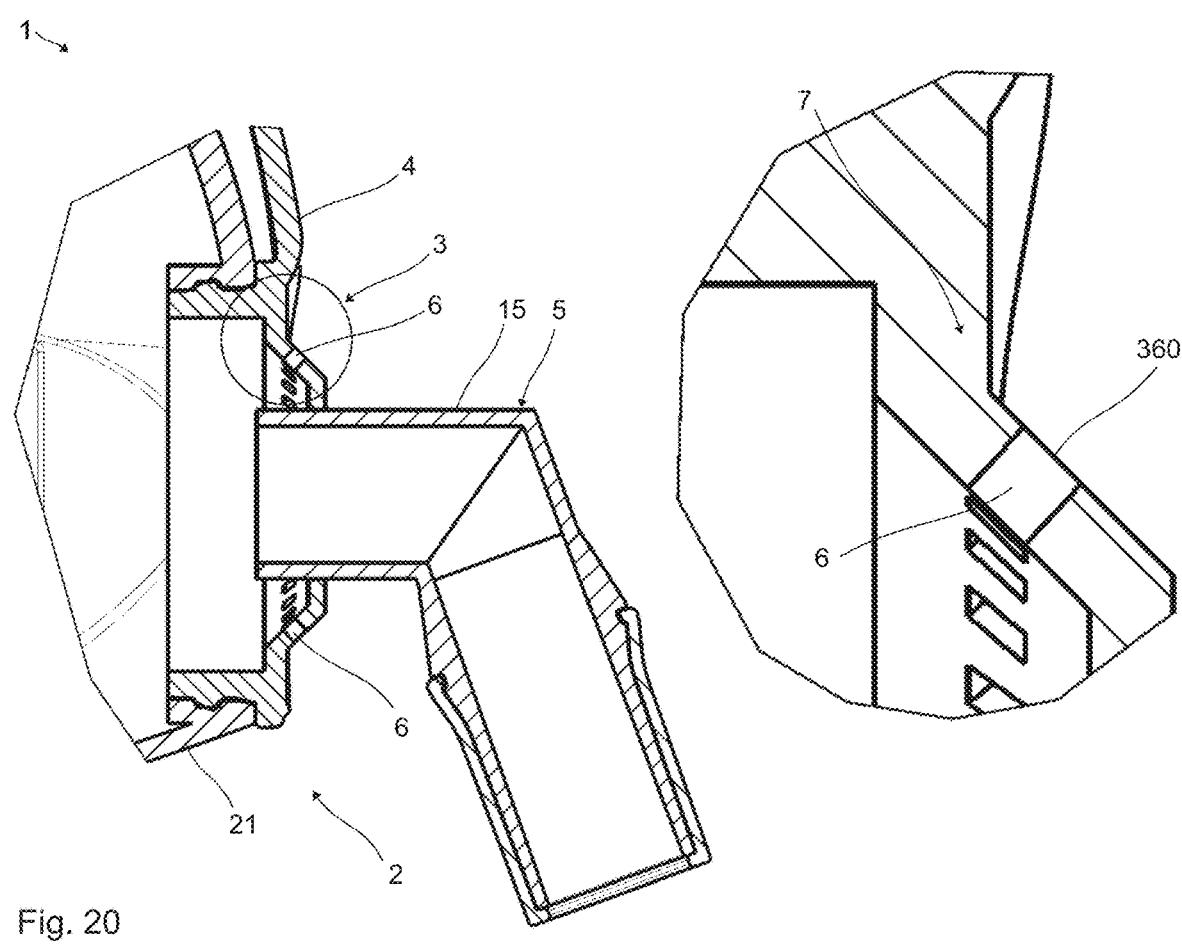
FIG. 20 shows the respiratory mask of FIG. 19 in a sectional side view with an enlarged detail view.
Figure 21:
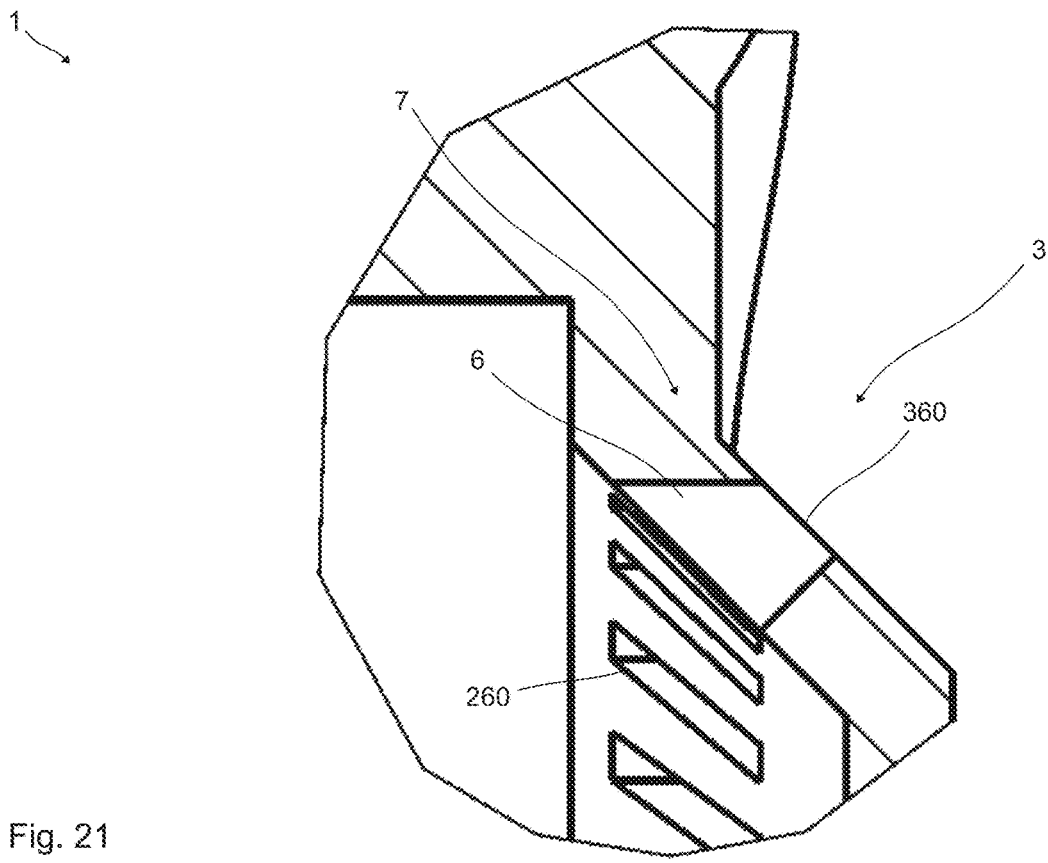
FIG. 21 shows one configuration of the respiratory mask of FIG. 19 in an enlarged detail view.
Figure 22:
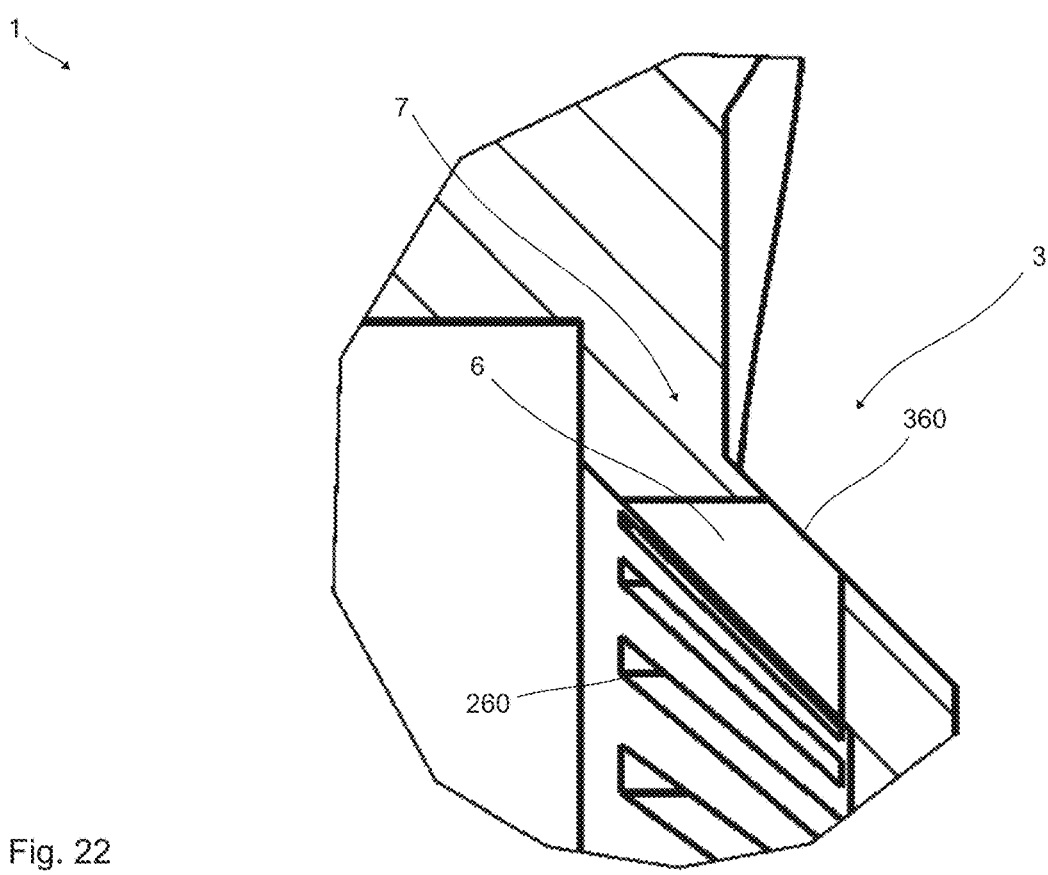
FIG. 22 shows another configuration of the respiratory mask of FIG. 19 in an enlarged detail view.

Advantageous configurations of the emission device 3 of the respiratory mask 1 shown in FIG. 19 are shown in enlarged detail representations in FIG. 21 and FIG. 22.

Figure 23:
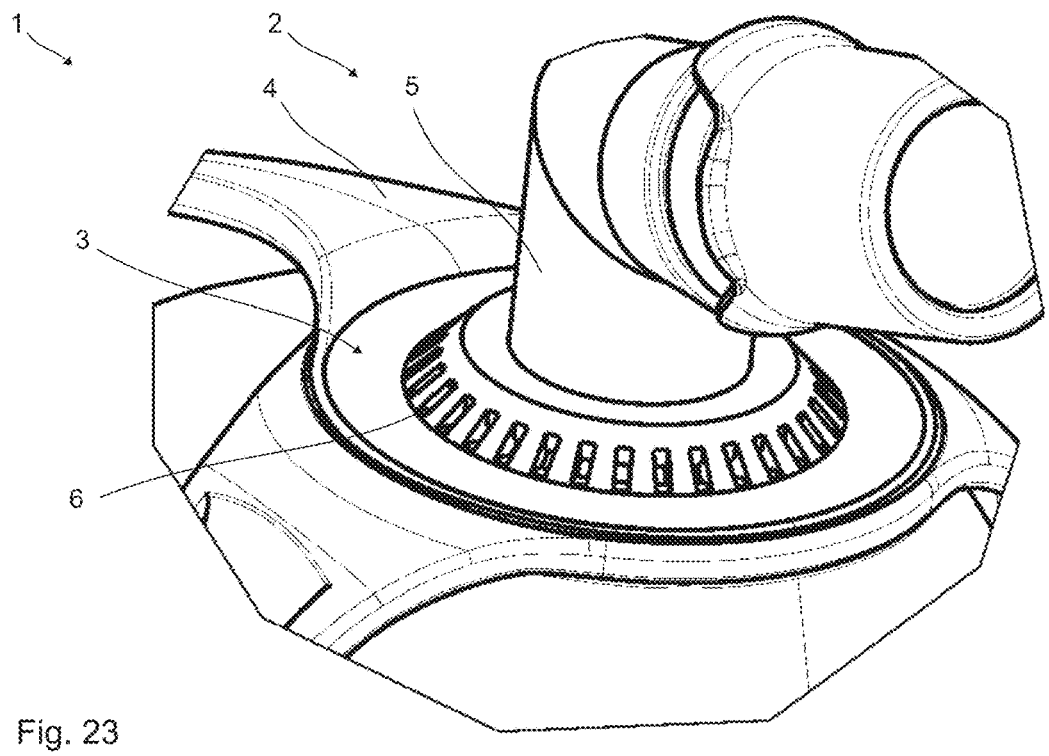
FIG. 23 shows a respiratory mask in a perspective detail view.
Figure 24:
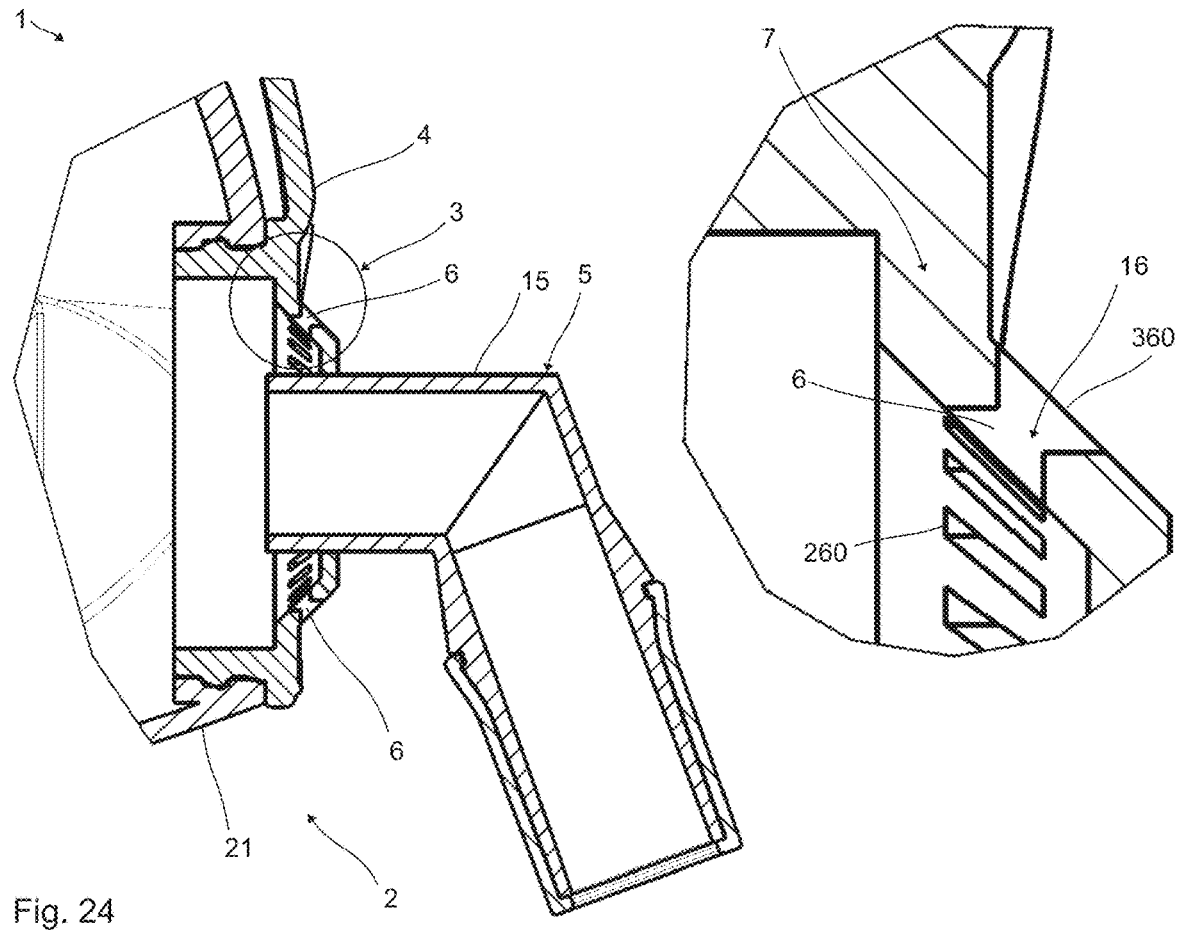
FIG. 24 shows the respiratory mask of FIG. 23 in a sectional side view with an enlarged detail view.
Figure 25:
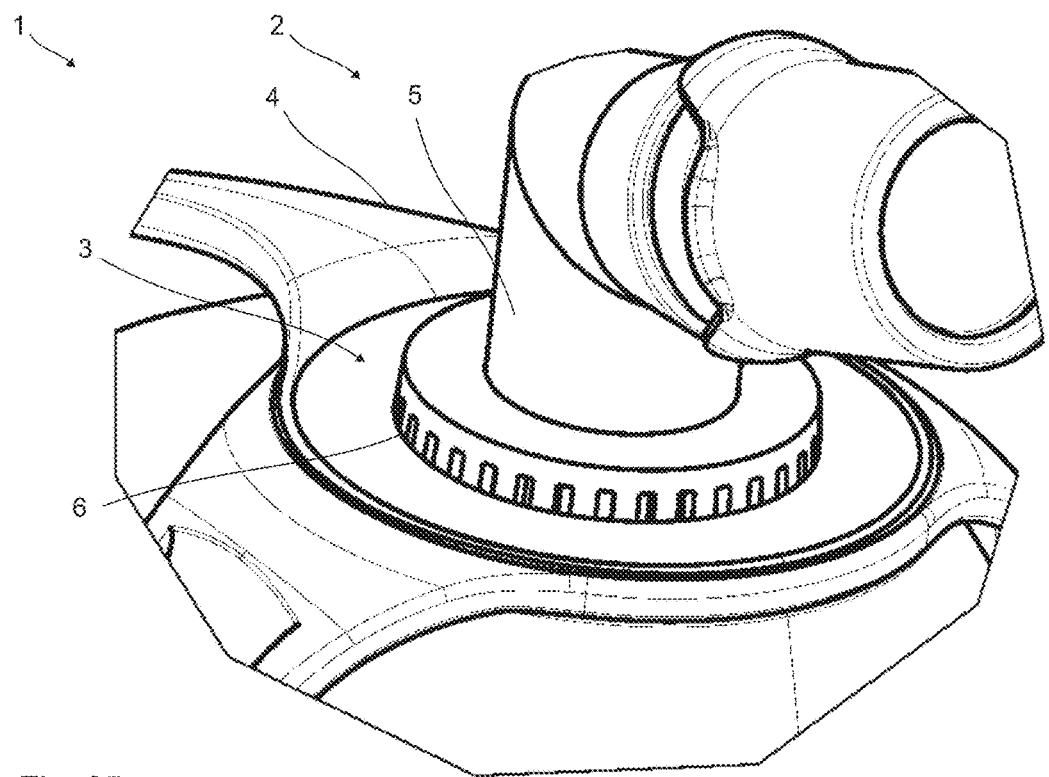
FIG. 25 shows a respiratory mask in a perspective detail view.
Figure 26:
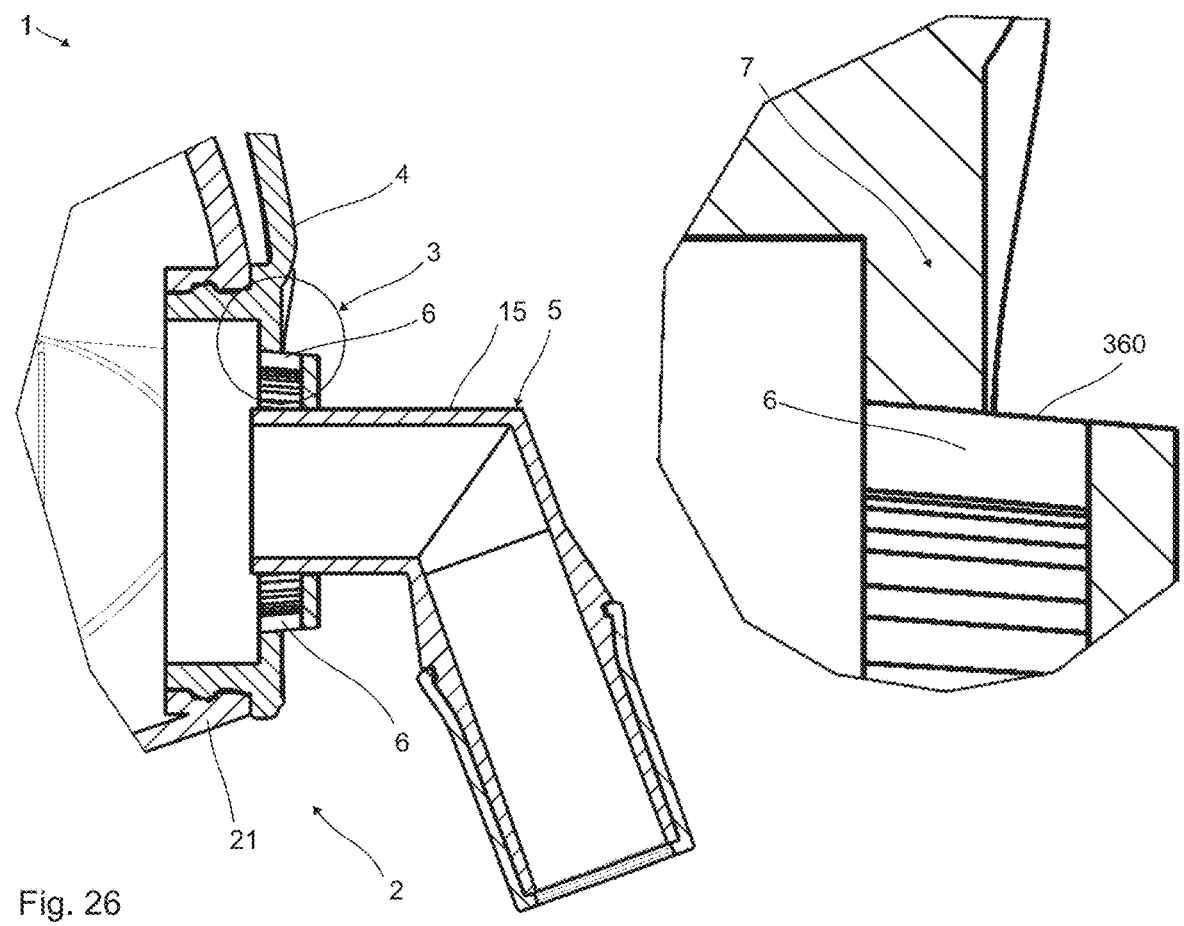
FIG. 26 shows the respiratory mask of FIG. 25 in a sectional side view with an enlarged detail view.

FIG. 23 and FIG. 25 respectively show one configuration of the respiratory mask 1 according to the invention. FIG. 24 and FIG. 26 in this case respectively show a sectional detail representation of FIGS. 23 and 25, the circularly bordered region being represented on an enlarged scale in the right-hand half of the image.

FIG. 27 shows casting tools 9 for the process according to the invention for producing the respiratory mask 1. In order to produce the flow subchannel 7, in this case two mutually complementary casting tools 9 are used. The emission device 3 is, for example, in this case manufactured by injection molding. Each casting tool 9 is in this case equipped with respectively two projections 19. The projections are in this case, for example, configured conically.

During the casting, a projection 19 of one casting tool 9 in each case extends respectively with a projection 19 of the other casting tool 9 into a common flow channel 6. By the casting tools 9 and projections 19 shown here, mold releases are manufactured in the region of the flow channels 6, with a profile which offers particularly favorable flow properties.

By the mold releases, removal of the emission device 3 is not blocked with a form fit despite the flow subchannel 7.

In this case, the emission device 3 may be manufactured in one casting process together with the mask unit 2 and, for example, with the mask body 4 or the connection unit 5. It is, however, also possible for the emission device 3 to be manufactured as an initially separate cast part 13 in its own casting process. Subsequently, the cast part 13 is placed in a further casting tool 9, where it is injection-overmolded. By the injection over-molding, the cast part 13 is connected to the mask unit 2 and, for example, to the mask body 4 or the connection unit 5.

FIG. 28 shows the casting tools 9 in an alternative configuration. The projections 19 are in this case configured in the shape of rods.

In one configuration, one or more casting tools 9 may also be equipped with retractable projections 19. In this case, the projections 19 protrude into one or more flow channels 6 during the casting. After the casting, the projections 19 may then be retracted so that removal of the emission device 3 is not blocked with a form fit despite the flow subchannel 7.

Figure 29:
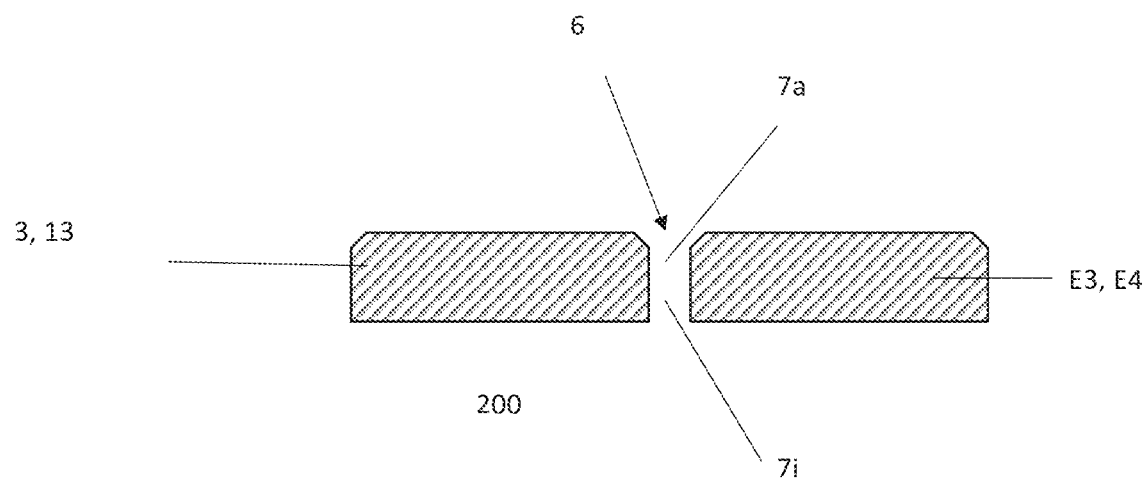
FIG. 29 shows a schematic representation of an emission device.

FIG. 29 shows the emission device 3 having at least one flow channel 6 which consists of at least two flow subchannels 7a, 7i. The flow subchannels 7a, 7i have, at least in sections, different geometries which are configured in such a way that they satisfy the technical requirements in terms of flow for the inner region 7i facing toward the patient 200 and the outer region 7a facing toward the ambient air. The flow subchannels 7a, 7i may be produced by a casting process with two mutually complementary casting tools 9 having differently configured projections 19.

The emission device 3 may be configured as part of the mask body 4 or of the connection unit 5, or manufactured as a separate component which, however, is integrated into the mask body/the connection unit. The emission device 3 forms a plane E3, and the mask body/the connection unit forms a plane E4. The planes E3 and E4 are, for example, perpendicular to one another. The planes E3 and E4 may be at a distance from one another or may coincide. The planes E3 and E4 may extend inclined to one another or parallel to one another. If the planes E3 and E4 are at a distance from one another, they are materially connected to one another by a shoulder or a connecting piece 28. The flow channels 6 may be arranged in the shoulder. The shoulder may have any desired inclinations and, for example, connect the planes E3 and E4 with a curvature or a straight line. The flow direction is also determined by the inclination of the shoulder.

FIG. 29 shows that the two mutually complementary casting tools 9 must comprise differently configured projections 19, since these form differently configured flow subchannels 7a, 7i, which together form the flow channel 6.

The emission device 3 of FIG. 29 may for example be used in a respiratory mask having at least one mask unit 2, the mask unit 2 comprising at least one mask body 4 and at least one connection unit 5 which can be connected to the mask body 4 for connection of a respiratory gas feed line 101, and the emission device being equipped with a multiplicity of flow channels 6, and the flow channels 6 in the emission device being produced in a casting process with at least two mutually complementary casting tools 9, each having at least one projection 19 protruding at least partially into the flow channel 6 during the casting.

Figure 30:
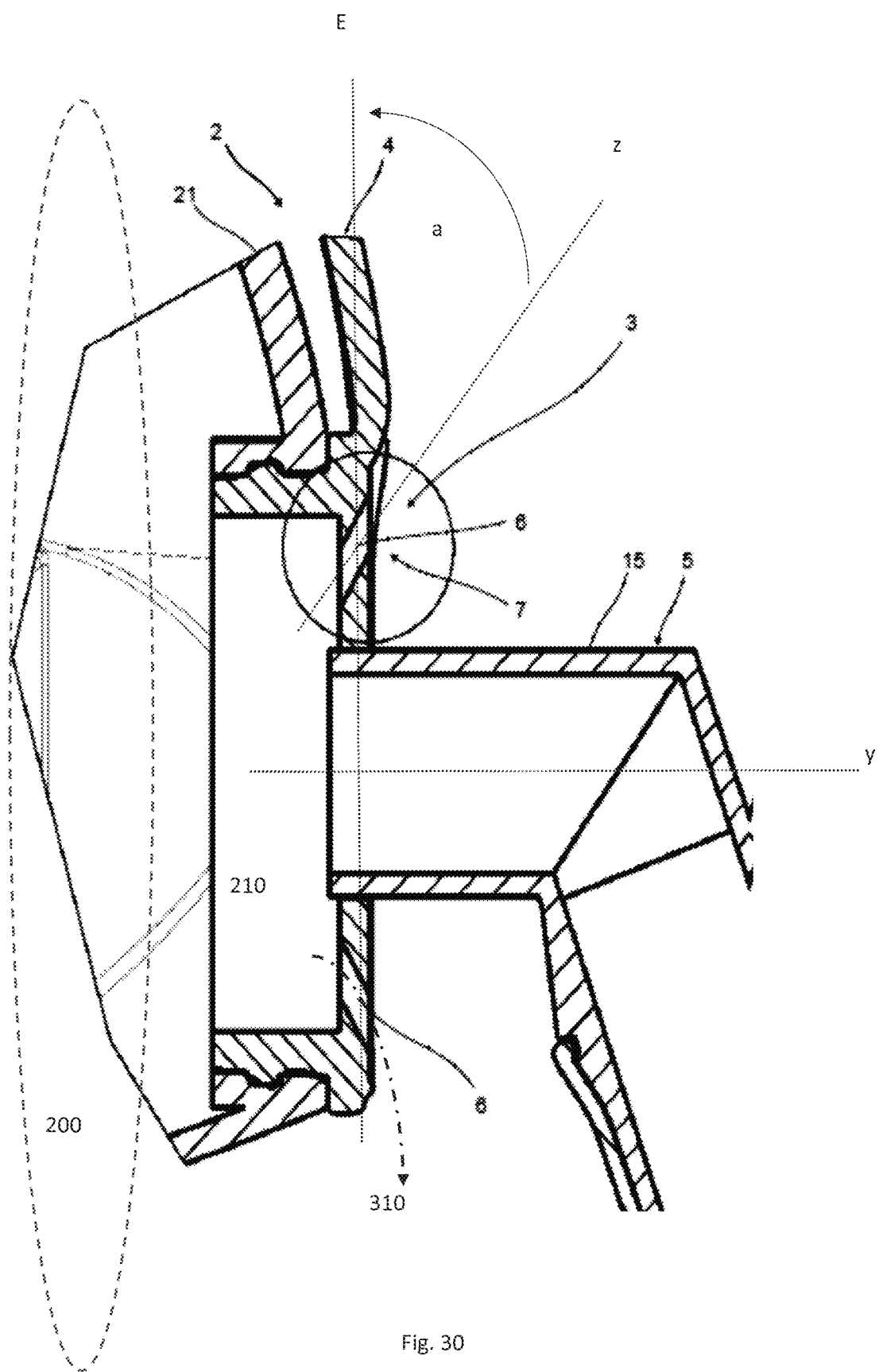
FIG. 30 shows a schematic representation of a respiratory mask having an emission device on the face of a patient.
Figure 31:
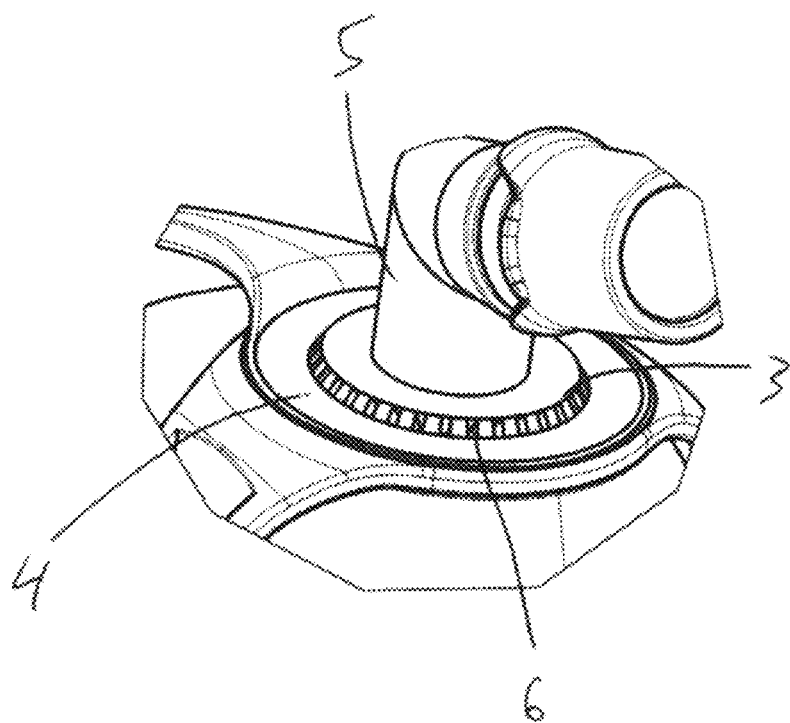
FIGS. 31-34 show various schematic representations of respiratory masks with different emission devices and flow channels, corresponding to FIGS. 23-26.
Figure 31:
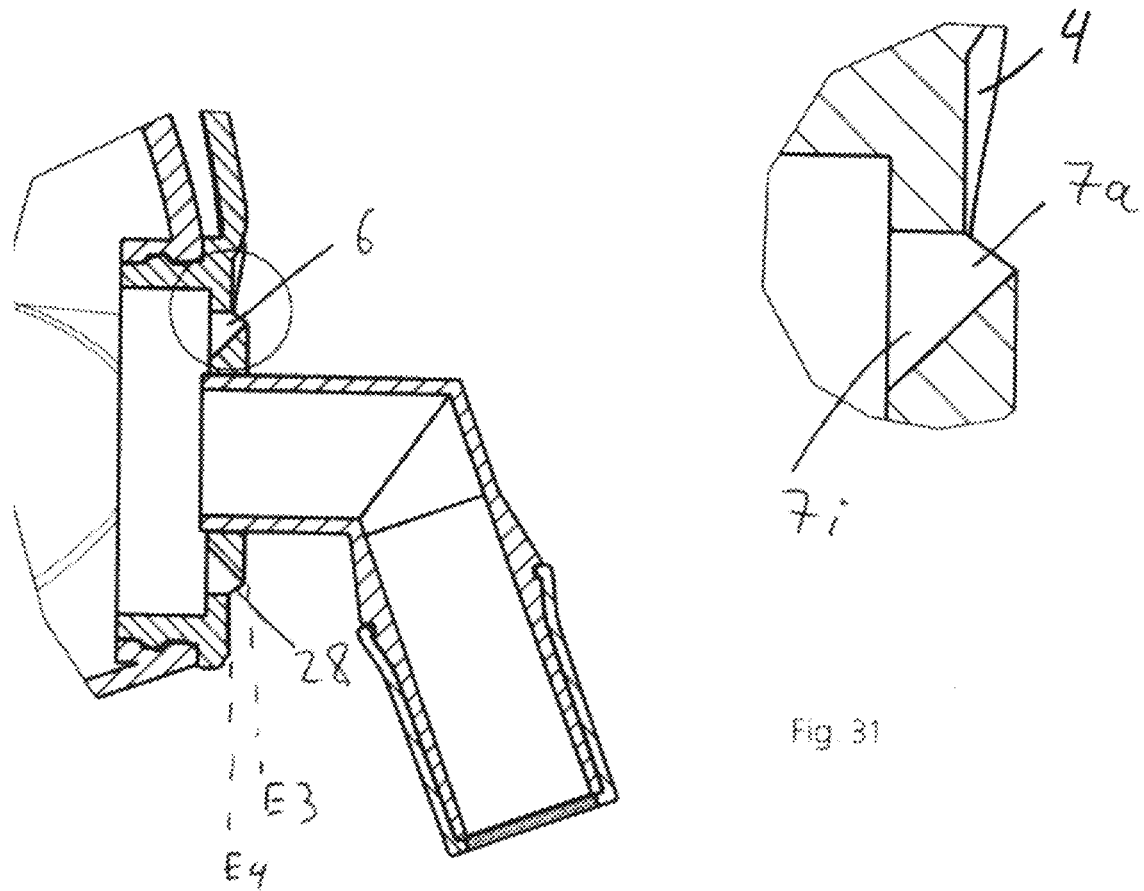

FIG. 30 shows a respiratory mask 1 having a mask unit 2 and having at least one emission device 3 for discharging exhaled gas from inside the respiratory mask 1, wherein the mask unit comprises at least one mask body 4 and at least one connection unit 5 connected to the mask body 4 for connection of a respiratory gas feed line 101 and wherein the emission device 3 comprises a multiplicity of separate flow channels 6, which are arranged next to the connection unit 5 in the mask body 4, the emission device 3 comprising at least nine separate flow channels 6, which respectively consist of at least two flow subchannels 7, 7a, 7i, the flow channels 6 being arranged at a distance from one another and next to or in the connection unit 5. The flow subchannels 7, 7a, 7i may be configured identically or differently.

In an operating state, the respiratory mask 1 is placed with the mask plate 21 in a leak-tight fashion on the face of a patient 200 while essentially maintaining a positive pressure inside the respiratory mask on the side facing toward the patient, the emission device 3 discharging exhaled gas at a positive pressure by means of the flow channels 6 from inside 210 the respiratory mask 1 to the ambient air 310.

With the arrangement of the emission device, the respiratory mask 1 defines a plane E perpendicular to the axis y of the connection device, the axis y of the connection device for example pointing perpendicularly away from the face of the patient in a working state on the patient. Here, perpendicularly means in an angle range of 70-120° relative to a plane which spans the face. With their flow direction, the flow channels 6 respectively define a plane z, for example by the region of their smallest cross section, the planes E and z being arranged at an angle a of between about 20 and 100°, preferably between about 45 and 90°, with respect to one another.

FIGS. 31-34 show the respiratory mask 1 having a mask unit 2 and having at least one emission device 3 for discharging exhaled gas from inside the respiratory mask 1, wherein the mask unit 2 comprises at least one mask body 4 and at least one connection unit 5 connected to the mask body 4 for connection of a respiratory gas feed line 101 and wherein the emission device 3 comprises a multiplicity of separate flow channels 6, which are arranged next to the connection unit 5 in the mask body 4, the emission device 3 comprising at least nine separate flow channels 6, which respectively consist of at least two flow subchannels 7, 7a, 7i, the flow channels 6 being arranged at a distance from one another and at least in sections circularly around the connection unit 5.

The emission device 3 may be formed integrally as a part of the mask body 4 or of the connection unit. The emission device 3 may also be manufactured as a separate component 3 which, however, is integrated into the mask body or the connection unit. The emission device 3 would then be replaceable. Emission devices 3 having different characteristic curves could thus be used for a mask.

Figure 34:
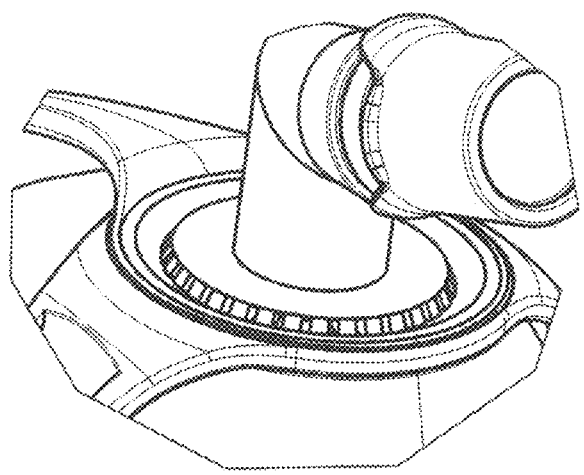
Figure 34:
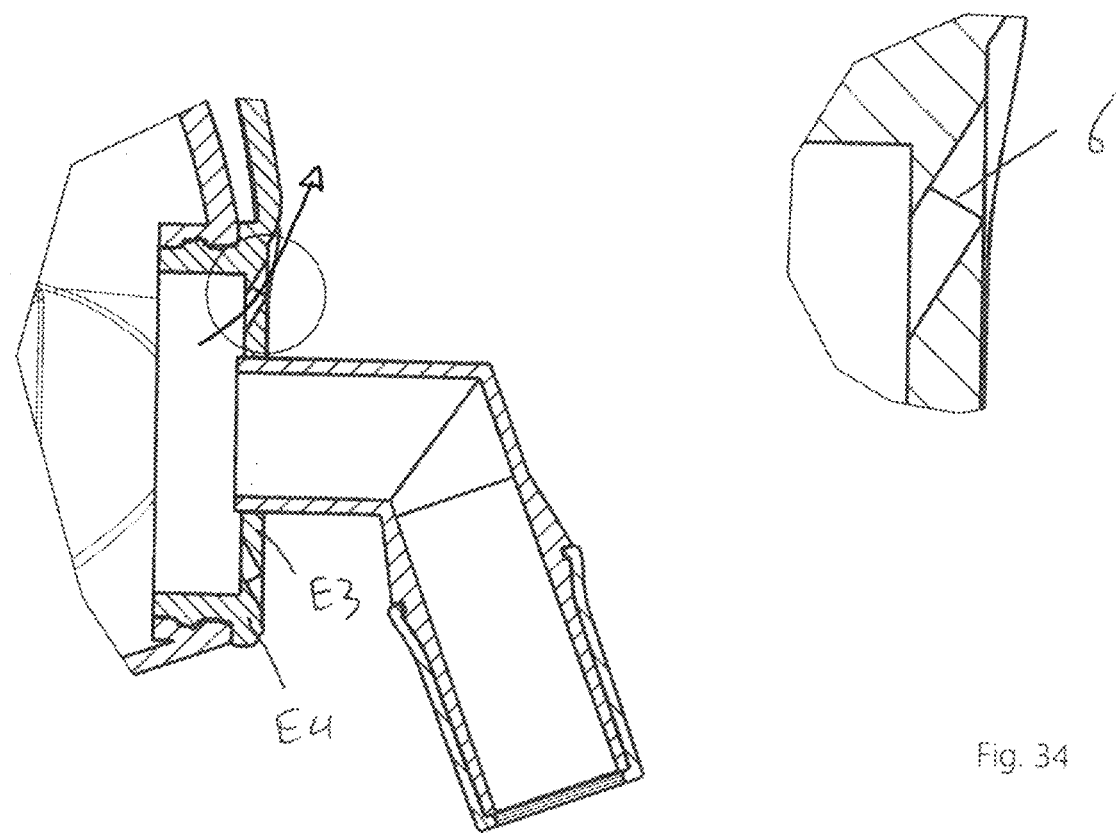

The emission device 3 forms a plane E3, and the mask body or the connection unit forms a plane E4. The planes E3 and E4 may be at a distance from one another (FIG. 31 and FIG. 32) or may coincide (FIG. 34). The planes E3 and E4 may extend inclined to one another or parallel to one another. If the planes E3 and E4 are at a distance from one another, they are materially connected to one another by a shoulder 28. The flow channels 6 may be arranged in the shoulder 28. The shoulder may have any desired inclinations and, for example, connect the planes E3 and E4 with a curvature or a straight line. The flow direction is also determined by the inclination of the shoulder.

Figure 32:
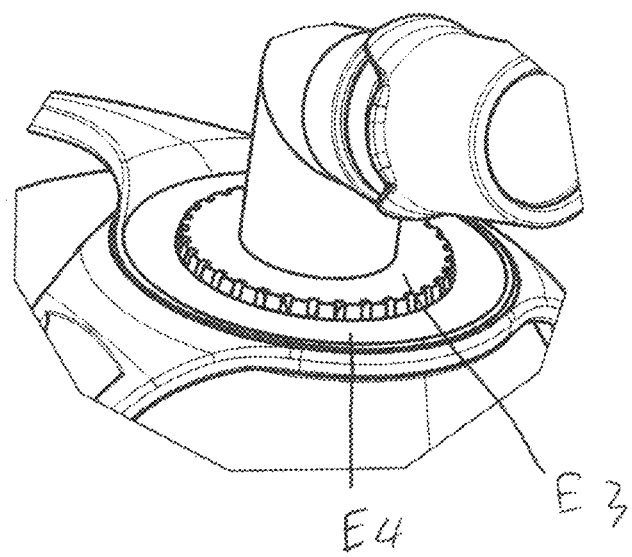
Figure 32:
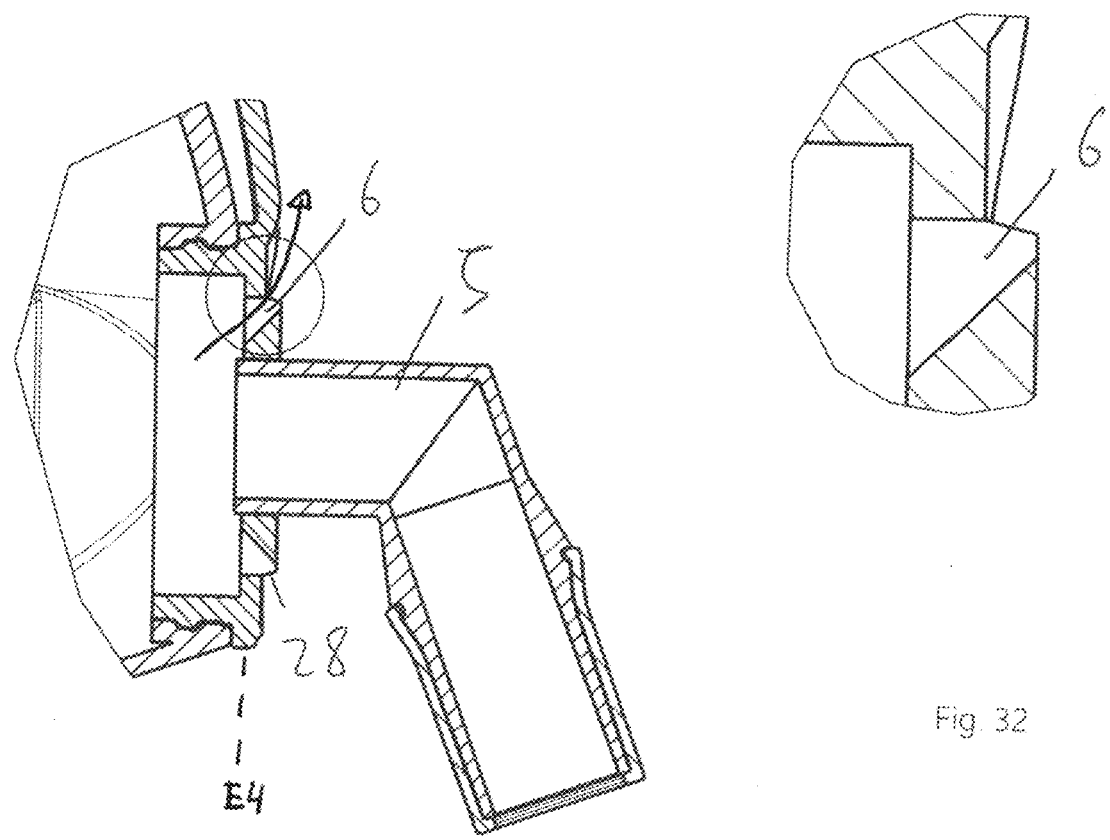
Figure 33:
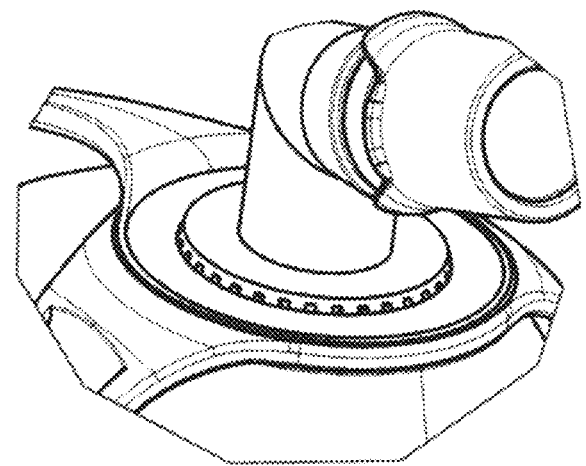
Figure 33:
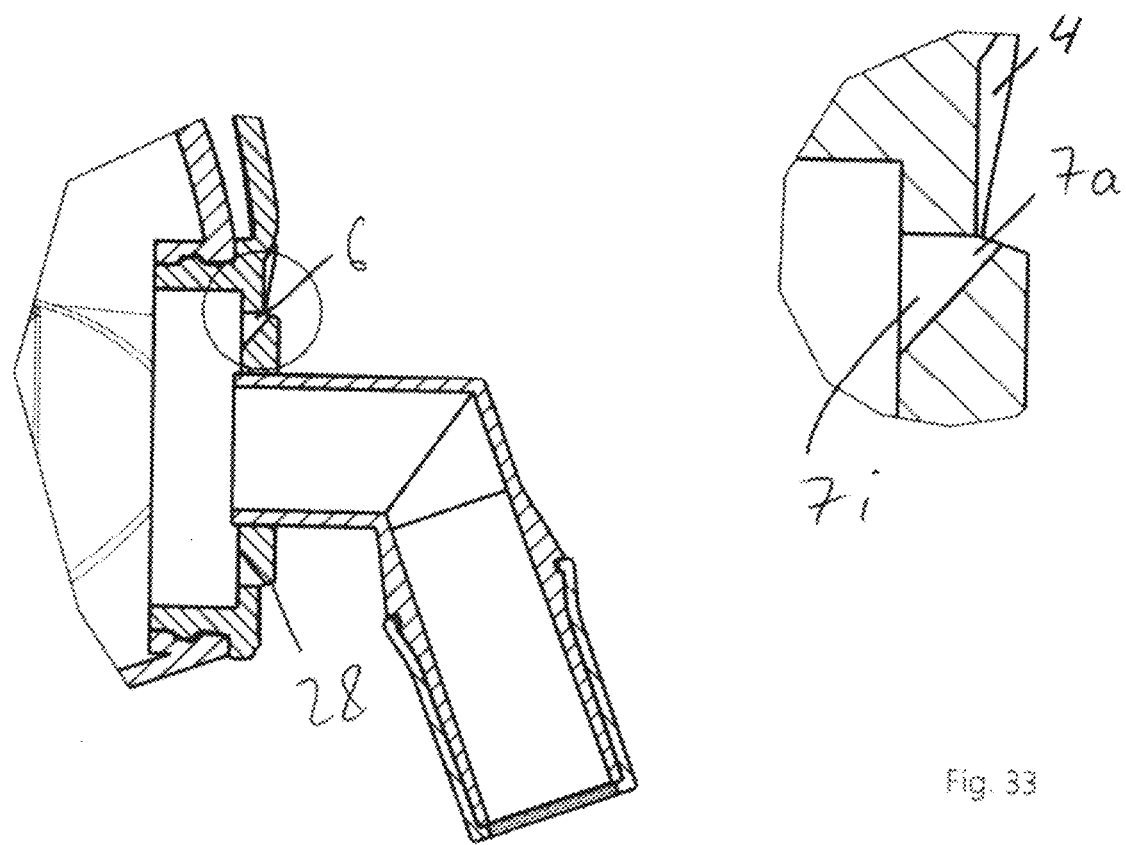

Next to the flow channels 6 or the flow subchannel 7a, the surface of the mask body 4 comprises a flow guide surface 4, which is for example inclined in such a way that the respiratory gases flowing out are diverted optimally from the patient. In FIG. 32 and FIG. 34, the respiratory gases flowing out are illustrated by an arrow.

LIST OF REFERENCE NUMERALS 1 respiratory mask
2 mask unit
3 emission device
4 mask body
5 connection unit
6 flow channel
7, 7a, 7i flow subchannel
8 arrangement
9 casting tool
11 forehead support
13 cast part
15 angle piece
16 constriction section
19 projection
21 mask bead
26 inlet region
28 shoulder
36 outlet region
100 respirator apparatus
101 respiratory gas feed line
160 constriction
200 face of the patient
210 inner region of the respiratory mask
260 inlet opening
310 ambient air
360 outlet opening

What is claimed is:

1. A respiratory mask, wherein the mask comprises a mask unit and at least one emission device for discharging exhaled gas from inside the respiratory mask, the mask unit comprising at least one mask body and at least one mask bead connected to the mask body and a connection unit connected to the mask body for connection of a respiratory gas feed line, and the emission device comprising a plurality of separate flow channels which respectively consist of at least two flow subchannels and are arranged at a distance from one another and at least in sections circularly or semicircularly, and wherein at least one of the flow channels comprises at least one constriction section which extends over a distance which is at least equal to one half of a total length of the flow channel; and at least one of the flow channels comprises at least one inlet region narrowing in the shape of a funnel before a constriction section in a flow direction and at least one outlet region widening in the shape of a funnel after the constriction section in the flow direction.

2. The respiratory mask of claim 1, wherein the emission device is arranged in the mask body or in the connection unit.

3. The respiratory mask of claim 1, wherein the emission device is arranged at an interface between the mask body and the connection unit.

4. The respiratory mask of claim 1, wherein the emission device is formed integrally as a part of the mask body or of the connection unit.

5. The respiratory mask of claim 1, wherein the emission device is manufactured as a separate component which is integrated into the mask body or the connection unit.

6. The respiratory mask of claim 1, wherein the emission device defines a plane E3 and the mask body or the connection unit defines a plane E4.

7. The respiratory mask of claim 6, wherein the planes E3 and E4 are at a distance from one another or coincide.

8. The respiratory mask of claim 6, wherein the planes E3 and E4 are at a distance from one another and are materially connected to one another by a shoulder, the flow channels being arranged in the shoulder.

9. The respiratory mask of claim 1, wherein the emission device comprises at least nine separate flow channels which respectively consist of at least two flow subchannels, the flow channels being arranged at a distance from one another and at least in sections circularly around the connection unit.

10. The respiratory mask of claim 1, wherein the connection unit is connected rotatably to the mask body and wherein the emission device comprises a plurality of separate flow channels which are arranged next to the connection unit in the mask body, the emission device comprising a plurality of separate flow channels which respectively consist of at least two flow subchannels, the flow channels being arranged at a distance from one another and at least in sections circularly around the connection unit.

11. The respiratory mask of claim 1, wherein the emission device defines a plane E perpendicular to an axis y of the connection unit and the flow channels respectively define a plane z of an emission direction, the planes E and z being arranged at an angle of between about 20 and 100° with respect to one another.

12. The respiratory mask of claim 1, wherein at least one of the flow channels has a varying channel cross section and/or at least two different channel cross sections.

13. The respiratory mask of claim 1, wherein at least one of the flow channels is configured at least in sections conically and/or in the shape of a cone.

14. The respiratory mask of claim 1, wherein at least one shoulder is arranged in at least one of the flow channels.

15. The respiratory mask of claim 1, wherein at least one of the flow channels comprises at least in sections a channel cross section with a quadrilateral cross-sectional profile.

16. The respiratory mask of claim 1, wherein the flow channels are inclined at an angle of between about 10° and 50° with respect to a common symmetry axis, so that an emission direction toward an edge region of the respiratory mask is formed and/or the longitudinal axes of the flow channels intersect at a common point and/or at least one of the flow channels comprises an outlet opening which is arranged transversely with respect to an inlet opening, so that a flow of the exhaled gas is diverted before emerging from the respiratory mask.

17. A process for producing a respiratory mask comprising a mask unit and at least one emission device for discharging exhaled gas from inside the respiratory mask, the mask unit comprising at least one mask body and at least one mask bead connected to the mask body and a connection unit connected to the mask body for connection of a respiratory gas feed line, and the emission device comprising a plurality of separate flow channels which respectively consist of at least two flow subchannels and are arranged at a distance from one another and at least in sections circularly or semicircularly, wherein at least the emission device is produced in a casting process with at least two mutually complementary casting tools, each having at least one projection protruding at least partially into a flow channel during casting, and wherein the process results in the respiratory mask of claim 1.

18. A process for producing a respiratory mask, wherein the flow channels are arranged in at least one part of the mask unit and wherein at least the emission device is produced in a casting process with at least two mutually complementary casting tools, each having at least one projection protruding at least partially into a flow channel during casting, and wherein the process results in the respiratory mask of claim 1.

\* \* \* \* \*